US007141590B2

(12) United States Patent
Cutshall et al.

(10) Patent No.: US 7,141,590 B2
(45) Date of Patent: Nov. 28, 2006

(54) PHARMACEUTICAL USES AND SYNTHESIS OF NICOTINANILIDE-N-OXIDES

(75) Inventors: Neil S Cutshall, Everett, WA (US); Kraig M Yager, Snohomish, WA (US)

(73) Assignee: UCB SA, Slough (GB)

( * ) Notice: Subject to any disclaimer, the term of this patent is extended or adjusted under 35 U.S.C. 154(b) by 0 days.

(21) Appl. No.: 10/015,861

(22) Filed: Dec. 12, 2001

(65) Prior Publication Data

US 2003/0004189 A1    Jan. 2, 2003

Related U.S. Application Data

(60) Provisional application No. 60/258,730, filed on Dec. 29, 2000.

(51) Int. Cl.
*A61K 31/4412*  (2006.01)
*C07D 211/94*  (2006.01)

(52) U.S. Cl. ...................... 514/358; 546/347
(58) Field of Classification Search ............... 546/347; 514/358
See application file for complete search history.

(56) References Cited

U.S. PATENT DOCUMENTS

| | | | | |
|---|---|---|---|---|
| 3,637,716 A | | 1/1972 | Bimber et al. ........ | 260/295 R |
| 3,766,195 A | | 10/1973 | Bimber et al. ........ | 260/295 R |
| 3,950,160 A | | 4/1976 | Abu El-Haj et al. ....... | 71/92 |
| 4,055,427 A | * | 10/1977 | Bergthaller et al. ...... | 106/150.1 |
| 4,730,051 A | * | 3/1988 | Ueda et al. ............ | 546/291 |
| 4,787,931 A | * | 11/1988 | Henrie et al. ........... | 504/167 |
| 4,978,385 A | * | 12/1990 | Yagihara et al. ......... | 504/178 |
| 4,990,503 A | | 2/1991 | Khanna et al. .......... | 514/303 |
| 5,472,687 A | | 12/1995 | Proctor ............... | 424/70.1 |
| 6,022,884 A | | 2/2000 | Mantlo et al. .......... | 514/352 |
| 6,333,341 B1 | | 12/2001 | Mantlo et al. .......... | 514/336 |
| 6,794,397 B1 | * | 9/2004 | Cai et al. .............. | 514/344 |

FOREIGN PATENT DOCUMENTS

| | | |
|---|---|---|
| DE | 2538950 A | 3/1977 |
| GB | 1134651 | 11/1968 |
| WO | WO 98/07692 | 2/1998 |
| WO | WO 99/07380 | 2/1999 |
| WO | WO 99/62885 | 12/1999 |
| WO | WO 01/14340 | 3/2001 |
| WO | WO 01/55115 | 8/2001 |
| WO | WO 02/22599 | 3/2002 |

OTHER PUBLICATIONS

Caplus, English Abstract DN 81:169412, Schnekenburger, Joerg et al 1974.*
English Abstract, Caplus DN 75:75600 Intramolecular hydrogen bond . . . by Mirek, Julian et al (1971), 45(2), 205-900.*
English Abstract, Caplus, DN 128:289722, Structure and anti-inflammatory . . . Bukhtiarova, T. A.et al (1997), 31(11), 30-32.*
English Abstract DN 133:135326, Preparation of amide . . . , Miyahara, Osamu et , JP 2000226372, Aug. 15, 2000.*
DN 132:22963, Preparation of N-(pyrazolylphenyl)alkanamides and analogs as IL-2 production inhibitors, Betageri, Rajashekhar et al, WO 9962885, Dec. 9, 1999.*
Caplus English abstract DN 127:331402, Preparation of pyridine-2,3-dicarboxamides.., Tonishi, Masanori et al .EP 799825 A1, Oct. 8, 1997.*
DN 127:51002. WO 9717070, Sebti Said et al, May 15, 1997.*
JP 63017811 Yagihara, Hiromu. English Abstract DN 109:68852, Jan. 25, 1988.*
English Abstract DN 97:215892 Penicillin derivs. and their salts JP 57109792, Jul. 8, 1982.*
English abstract DN 87:5812, SU 539878, 1976, Otkrytiya, Izobret. Et al, Dec. 25, 1976.*
Danilenko, G. I. Antiinflammatory action . . . English abstract DN 89:89560. 1976.*
Ca plus English abstract 110:154162 EP 292990. Yagihara, Hiroshi et al, Nov. 30, 1988.*
Caplus , English Abstract DN 86:15920 Brzezinski Bogumil 1976.*
Caplus , English Abstract DN 83:96958 Brzezinski B et al 1975.*
Caplus English Abstract DN 97:144206 Brzezinski wt al 1982.*
Santamaria Babi et al., "The interleukin-8 receptor B and CXC chemokines can mediate transendothelial migration of human skin homing T cells," *Eur. J. Immunol.* 26(9):2056-2061, Sep. 1996.
Besemer et al., "Specific binding, internalization, and degradation of human neutrophil activating factor by human polymorphonuclear leukocytes," *J. Biol. Chem.* 264(29):17409-17415, Oct. 15, 1989.
Boisvert et al., "A leukocyte homologue of the IL-8 receptor CXCR-2 mediates the accumulation of macrophages in atherosclerotic lesions of LDL receptor-deficient mice," *J. Clin. Invest.* 101(2):353-363, Jan. 15, 1998.
Chuntharapai et al., "Monoclonal antibodies detect different distribution patterns of IL-8 receptor A and IL-8 receptor B on human peripheral blood leukocytes," *J. Immunol.* 153(12):5682-5688, Dec. 15, 1994.
Chuntharapai et al., "Regulation of the expression of IL-8 receptor A/B by IL-8: possible functions of each receptor," *J Immunol* 155(5):2587-2594, Sep. 1, 1995.
Cummings et al., "Expression and function of the chemokine receptors CXCR1 and CXCR2 in sepsis," *J. Immunol.* 162(4):2341-6, Feb. 15, 1999.
Donnelly Robertson, "Mediators, mechanisms and mortality in major trauma," *Resuscitation* 28(2):87-92, Oct. 1994.

(Continued)

*Primary Examiner*—Rita J. Desai
(74) *Attorney, Agent, or Firm*—Jane E. R. Potter; Davis Wright Tremaine LLP

(57) ABSTRACT

Disclosed are nicotinanilide-N-oxide compounds, methods for their production, pharmaceutical compositions which include these compounds, and methods for their use in various therapies.

4 Claims, No Drawings

OTHER PUBLICATIONS

Donnelly and Robertson, "Trauma, inflammatory cells and ARDS," *Arch. Emerg. Med.* 10(2):108-11, Jun. 1993.

Endo et al., "Elevation of interleukin-8 (IL-8) levels in joint fluids of patients with rheumatoid arthritis and the induction by IL-8 of leukocyte infiltration and synovitis in rabbit joints," *Lymphokine and Cytokine Research* 10(4):245-252, Aug. 1991.

Fuhlendorff et al., "[Leu$^{31}$, Pro$^{34}$]Neuropeptide Y: a specific $Y_1$ receptor agonist," *PNAS USA* 87(1):182-186, Jan. 1990.

Gillitzer et al., "Differential expression of GRO-alpha and IL-8 mRNA in psoriasis: a model for neutrophil migration and accumulation in vivo," *J. Invest. Dermatol.* 107(5):778-782, Nov. 1996.

Goldman et al., "Tumor Necrosis Factor-α Mediates Acid Aspiration-induced Systemic Organ Injury," *Ann. Surg.* 212(4):513-520, Oct. 1990.

Goodman et al., "Inflammatory cytokines in patients with persistence of the acute respiratory distress syndrome," *Am. J. Respir. Crit. Care Med.* 154(3 Pt 1):602-611, Sep. 1996.

Grob et al., "Characterization of a receptor for human monocyte-derived neutrophil chemotactic factor/interleukin-8," *J. Biol. Chem.* 265(14):8311-8316, May 15, 1990.

Hammond et al., "IL-8 induces neutrophil chemotaxis predominantly via type I IL-8 receptors," *J. Immunol.* 155(3):1428-1433, Aug. 1, 1995.

Holmes et al., "Structure and functional expression of a human interleukin-8 receptor," *Science* 253(5025):1278-1280, Sep. 13, 1991.

Horuk et al., "Expression of chemokine receptors by subsets of neurons in the central nervous system," *J. Immunol.* 158(6):2882-2890, Mar. 15, 1997.

Izzo et al., "Interleukin-8 and neutrophil markers in colonic mucosa from patients with ulcerative colitis," *Am. J. Gastroenterology* 87(10):1447-1452, Oct. 1992.

Jones et al., "Chemokine antagonists that discriminate between interleukin-8 receptors. Selective blockers of CXCR2," *J. Biol. Chem.* 272(26):16166-16169, Jun. 27, 1997.

Kojima et al., "GRO-α mRNA is selectively overexpressed in psoriatic epidermis and is reduced by cyclosporin A in vivo, but not in cultured keratinocytes," *J. Invest. Dermatology* 101(6):767-772, Dec. 1993.

Linas et al., "Neutrophils accentuate ischemia-reperfusion injury in isolated perfused rat kidneys," *Am. J. Physiology* 255(4 Pt 2):F728-F735, Oct. 1988.

Mahida et al., "Enhanced synthesis of neutrophil-activating peptide-1/interleukin-8 in active ulcerative colitis," *Clinical Science* (London) 82(3):273-275, Mar. 1992.

Matsukawa et al., "Involvement of growth-related protein in lipopolysaccharide-induced rabbit arthritis: cooperation between growth-related protein and IL-8, and interrelated regulation among TNFα, IL-1, IL-1 receptor antagonist, IL-8, and growth-related protein," *Laboratory Investigation* 79(5):591-600, May 1999.

Murphy and Tiffany, "Cloning of Complementary DNA Encoding a Functional Human Interleukin-8 Receptor," *Science* 253(5025):1278-1280. Sep. 13, 1991.

Quan et al., "Antibodies against the N-terminus of IL-8 receptor A inhibit neutrophil chemotaxis," *Biochemical Biophysical Research Communications* 219(2):405-411, Feb. 15, 1996.

Repine and Beechler, "Neutropils and Adult Respiratory Distress Syndrome: Two Interlocking Perspectives in 1991," *Am. Rev. Respir. Dis.* 144:251-252, 1991.

Samanta et al., "Identification and characterization of specific receptors for monocyte-derived neutrophil chemotactic factor (MDNCF) on human neutrophils," *J. Exp. Med.* 169(3):1185-1189, Mar. 1, 1989.

Samson et al., "The second extracellular loop of CCR5 is the major determinant of ligand specificity," *J. Biol. Chem.* 272(40):24934-24941, Oct. 3, 1997.

Schwartz et al., "Role of the GRO family of chemokines in monocyte adhesion to MM-LDL-stimulated endothelium," *J. Clin. Invest.* 94(5):1968-1973, Nov. 1994.

Sheikh et al., "Binding of monoiodinated neuropeptide Y to hippocampal membranes and human neuroblastoma cell lines," *J. Biol. Chem.* 264(12):6648-6654, Apr. 25, 1989.

Simpson and Hechtman, "Pulmonar Injury Following Sepsis," *Prog. Clin. Biol. Res.* 388:265-275, 1994.

Srikant and Heisler, "Relationship between receptor binding and biopotency of somatostatin-14 and somatostatin-28 in mouse pituitary tumor cells," *Endocrinology* 117(1):271-278, Jul. 1985.

Terkeltaub et al., "Chemokines and Atherosclerosis," *Curr. Opin. Lipidol.* 9(5):397-405, Oct. 1998.

Terkeltaub et al., "The murine homolog of the interleukin-8 receptor CXCR-2 is essential for the occurrence of neutrophilic inflammation in the air pouch model of acute urate crystal-induced gouty synovitis," *Arthritis. Rheum.* 41(5):900-909, May 1998.

Thermos and Reisine, "Somatostatin receptor subtypes in the clonal anterior pituitary cell lines AtT-20 and GH3," *Mol. Pharmacol.* 33(4):370-377, Apr. 1988.

Villard et al., "GRO alpha and interleukin-8 in Pneumocystis carinii or bacterial pneumonia and adult respiratory distress syndrome," *Am. J. Respir. Crit. Care Med.* 152(5 Pt 1):1549-54, Nov. 1995.

Wang et al., "Chemokines and their role in tumor growth and metastasis," *J. Immunol. Methods* 220(1-2):1-17, Nov. 1, 1998.

White et al., "Identification of a potent, selective non-peptide CXCR2 antagonist that inhibits interleukin-8-induced neutrophil migration," *J. Biol. Chem.* 273(17):10095-10098, Apr. 24, 1998.

Xia and Hyman, "Chemokines/chemokine receptors in the central nervous system and Alzheimer's disease," *J. Neurovirology* 5(1):32-41, Feb. 1999.

Xia et al., "Interleukin-8 receptor B immunoreactivity in brain and neuritic plaques of Alzheimer's disease," *Am. J. Pathol.* 150(4):1267-1274, Apr. 1997.

Xu et al., "Modulation of IL-8 receptor expression on purified human T lymphocytes is associated with changed chemotactic responses to IL-8," *J. Leukoc. Biol.* 57(2):335-342, Feb. 1995.

Bukhtiarova et al., "Possibilities for search for new analgesics in the series of arylamides o isonicotinic and nicotinic acids," Chemical Abstracts Services, STN Database Accession No. 131:237346, 1998.

Chambon et al., "Toxicity and pharmacodynamic properties of N,N-diethylnicotinamide N-oxide (Coramine N-oxide)," Chemical Abstracts Services, STN Database Accession No. 71:89704, 1969.

Klebanov et al., "Antiinflammatory activity of some new pyridine carboxylic acid derivatives," Chemical Abstracts Services, STN Database Accession No. 88:15765, 1977.

Streightoff et al., "Inhibition of bacteria by 5-fluoronicotinic acid and other analogs of nicotinic acid," *Chemical Abstracts* 58(5):Abstract No. 4836a, Mar. 4, 1963.

Wieland et al., "Syntheses of 4-substituted nicotinamides via the N-oxides," *Chemische Berichte* 96:266-274, 1963.

Wieland et al., "Syntheses of 4-substituted nicotinamides via the N-oxides," Chemical Abstracts Services, STN Database Accession No. 1963:66395, 1963.

Bouzard, D. et al., "Fluoronaphthyridines as Antibacterial Agents. 4. Synthesis and Structure-Activity Relationships of 5-Substituted-6-fluoro-7-(cycloalkylamino)-1,4-dihydro-4-oxo-1,8-naphthyridine-3-carboxylic Acids," *J. Med. Chem.* 35:518-525, 1992.

Chambers, R.D. et al., "Polyfluoroheterocyclic Compounds. Part V. Catalytic Reduction of Perfluoro- and Chlorofluoro-pyridines and the Preparation of Polyfluoropyridinecarboxylic Acids," *Journal of the Chemical Society*, pp. 5045-5048, 1965.

Coe and Rees, "Preparation and reactions of 2,3,4,6-tetrafluoropyridine and its derivatives," *Journal of Fluorine Chemistry* 101(1): 45-60, Jan. 2000.

Collie and Tickle, "Production of some nitro- and amido-oxylutidines, Part I" *Journal of the Chemical Society* 73:229-235, 1898.

Dornow and Hahmann, "Synthese von 2-Oxy-imidazolo-(5',4':2,3)-pyridinen. Synthesen stickstoffhaltiger Heterocyclen, XII. Mitteilung.," *Archiv Der Pharmazie* 290: 20-31, 1957.

Dornow and Hahmann, "Synthesis of N-containing heterocycles. XII. Synthesis of 2-hydroxy-1-imidazo[b]pyridines," *Chemical Abstracts*, Abstract No. 1957:56771, 1957. See Also *Archiv Der Pharmazie* 290: 20-31, 1957.

Lamm, G., "2,6-Dichloronicotinic acids," *Chemical Abstracts*, Abstract No. 1977:189730, 1977. See also DT2538950.

* cited by examiner

PHARMACEUTICAL USES AND SYNTHESIS OF NICOTINANILIDE-N-OXIDES

This application claims the benefit of U.S. Provisional Patent Application No. 60/258,730, filed Dec. 29, 2000, where this provisional application is incorporated herein by reference in its entirety.

TECHNICAL FIELD

The present invention relates to nicotinanilide N-oxide compounds useful as pharmaceutical agents, to methods for their production, to pharmaceutical compositions which include these compounds, and to methods for their use in various therapies.

BACKGROUND OF THE INVENTION

Chemotactic cytokines (chemokines) are a class of potent inflammatory mediators that have the potential to attract specific subsets of leukocytes to sites of inflammation. Chemokines are typically low-molecular-mass (7–9 kd) proteins that can be divided into four subfamilies (CCC or β-subfamily, CXC or α-subfamily, $CX_3C$) and are categorized by their primary amino acid structure. The CXC subfamily is characterized by the two conserved Cys residues (C) near the N-terminus and separated by an amino acid (X). Some of the CXC chemokines, of which IL-8 and GRO-α are representative, belong further to the ELR+ subfamily (Glu-Leu-Arg) and are important in the recruitment and activation of neutrophils via the CXCR1 and CXCR2 receptors.

The interaction of chemokines with specific cell populations is mediated by G-protein-coupled seven-transmembrane receptors (7TMR). Chemokine receptors can be classified into four groups (CR, CCR, CXCR, CX3CR) based upon their primary amino acid sequence. The CXCR1 receptor binds with high affinity to IL-8 and low affinity to NAP-2, ENA-78 (epithelial cell-derived neutrophil-activating factor), GRO-α, -β, and -γ, whereas, CXCR2 binds with high affinity to all of the mentioned CXC chemokines. Both CXCR1 and CXCR2 receptors are found primarily on neutrophils and a subset of T-cells. W. Holmes et al., *Science* 253:1278 (1991); P. Murphy et al., *Science* 253:1280 (1991); A. Chuntharapai et al., *J. Immunol.* 153:5682 (1994); L. Xu et al., *J. Leukocyte Biol.* 57:335 (1995).

CXCR1 and CXCR2 have been shown to mediate the responses to CXC chemokines in neutrophils (polymorphonuclear neutrophils; PMN) and are essential to the acute inflammatory response. P. Grob et al., *J. Biol. Chem.* 265:8311 (1990); J. Besemer et al., *J. Biol. Chem.* 264:17, 409 (1989); A. Samanta et al., *J. Exp. Med.* 169:1185 (1989); W. Holmes et al., *Science* 253:1280 (1991); P. Murphy et al., *Science* 253:1280 (1991). Although both receptors are involved in neutrophil chemotaxis, in vitro studies using human neutrophils have shown inconclusively if chemotaxis is mediated by one or both receptors. IL-8 induced chemotaxis studies using anti-receptor monoclonal antibodies in CXCR1 and CXCR2 cell lines have led to conflicting reports. J. Quan et al., *Biochem. Biophys. Res. Commun.* 219:405 (1996); A. Chuntharapai et al., *J. Immunol.* 155:2587 (1995); M. Hammond et al., *J. Immunol.* 155:1428 (1995). There is also evidence to indicate that the transendothelial migration of CLA+ T-cells is a CXCR2 mediated event. L. Santamaria-Babi et al., *Eur. J. Immunol.* 26:2056 (1996).

The role, in inflammatory disorders, of neutrophil chemotaxis mediated by the CXCR1 and CXCR2 receptors is generally accepted. It has been reported that neutrophils are implicated in the pathogenesis of the acute respiratory distress syndrome (ARDS) in patients with sepsis. J. Repine et al., *Am. Rev. Respir. Dis.* 144:251 (1991). A causal role of PMNs in the lung injury associated with trauma is also widely accepted. G. Goldman et al., *Ann. Surg.* 212:513 (1990); S. Linas et al., *Am. J. Physiol.* 255:F728 (1988); R Simpson et al., *Prog. Clin. Biol. Res.* 388:265 (1994); S. Donnelly, *Arch. Emerg. Med.* 10:108 (1993); S. Donnelly, *Resuscitation* 28:87 (1994). For example, sepsis-related ARDS patients have increased levels of IL-8, ENA-78, ad GRO-α in their bronchoalveolar lavage fluids. R. Goodman et al., *Am. J. Respir. Crit. Care Med.* 154:602 (1996); J. Villard, *Am. J. Respir. Crit. Care Med.* 152:1549 (1995). Additionally, it has been demonstrated that CXCR1 functions as the single dominant CXC chemokine receptor for neutrophil chemotaxis in patients with sepsis. C. Cummings, *J. Immunol.* 162:2341 (1999).

High levels of IL-8 and tissue neutrophil infiltration have been observed in the synovial tissues of rheumatoid arthritis patients (H. Endo, *Lymphokine Cytokine Res.* 10:245 (1991)). Evidence has been presented that GRO-α and IL-8 are important mediators involved in the recruitment of neutrophils in the early and late phase of lipopolysaccharide-induced (LPS) rabbit arthritis. A. Matsukawa et al., *Lab. Invest.* 79:591 (1999). The murine CXCR2 receptor has also shown to be necessary for neutrophilic inflammation in a mouse model of gouty synovitis. R. Terkeltaub et al., *Arthritis. Rheum.* 41:900 (1998).

CXC chemokines have attracted attention as being important in the development of atherosclerosis. R. Terkeltaub et al., *Curr. Opin. Lipidol.* 9:397 (1998). The role of CXCR1 and CXCR2 ligands on monocyte function in atherosclerosis in rabbits was published by D. Schwartz et al., *J. Clin. Invest.* 94:1968 (1994). Knockout mice that lacked CXCR2 expression had diminished lesion size. W. Boisvert et al., *J. Clin. Invest.* 101:353 (1998).

The involvement of the CXCR2 receptor in the pathological inflammatory response elicited by central nervous system (CNS) cells as related to Alzheimer's disease is also gaining significant attention. M. Xia et al., *J. Neurovirol.* 5:32 (1999). Reports have focused on the upregulation of CXCR2 expression on dystrophic neurites of senile plaques. M Xia et al., *Am. J. Pathol.* 150:1267 (1997); R. Horuk et al., *J. Immunol.* 158:2882 (1997).

High levels of IL-8 and neutrophil infiltration have been observed in the pathogenesis of a number of other disease indications. This includes ulcerative colitis (Y. Mahida, *Clin. Sci.* 82:273 (1992); R. Izzo, *Am. J. Gastroenterol* 87:1447 (1992)) and psoriasis (R. Gillitzer et al., *J. Invest. Dermatol.* 107:778 (1996); T. Kojima., *J. Invest. Dermatol* 101:767 (1993)). CXCR1 and CXCR2 chemokines and their roles in tumor growth and metastasis have been reviewed. J. Wang, *J. Immunol. Meth.* 220:1 (1998).

To date, a limited number of CXCR1 and CXCR2 antagonists have been reported. It was reported that a bis-aryl urea was able selectively inhibit CXCR2 and prevent neutrophil migration and chemotaxis in a rabbit model. J. White, *J. Biol. Chem.* 273:10095 (1998). Other CXCR1 and CXCR2 receptor antagonists have focused on NH2-terminal truncations and modifications of IL-8, GRO-α, and ELR motif. S. Jones et al., *J. Biol. Chem.* 272:16166. Murine neutrophil recruitment in vivo could also be inhibited via CXCR2 receptor blocking using a truncated human GRO-α analog.

There are currently no CXCR1 or CXCR2 receptor antagonist based therapies widely available.

There is a continued need for the treatment of diseases mediated by the CXCR1 and CXCR2 receptors. Small molecule antagonists of CXC receptors and their ligands such as GRO-α and IL-8 would be useful in the control of harmful inflammatory processes as well as important tools for the investigation of receptor-ligand interactions.

SUMMARY OF THE INVENTION

The present invention relates to novel nicotinanilide N-oxide compounds useful as pharmaceutical agents, to methods for their production, to pharmaceutical compositions which include these compounds and a pharmaceutical carrier, and to pharmaceutical methods of treatment. The compounds of the present invention are G-protein-coupled, seven transmembrane domain (7TM) receptor antagonists. In particular, the compounds of the invention are useful for the prophylaxis and treatment of diseases or conditions involving inflammation due to neutrophil chemotaxis mediated via the CXCR1 and CXCR2 receptors. This invention also relates to intermediates and processes useful in the preparation of such compounds.

In one aspect, the present invention provides a compound having the structure (I):

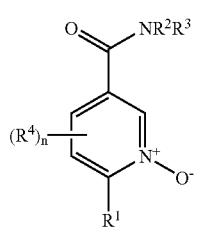

and optical isomers, diastereomers, enantiomers and pharmaceutically acceptable salts thereof, wherein $R^1$ is selected from $R^5$ and $R^5$—$(C_1$–$C_6$heteroalkylene)- where $R^5$ is selected from hydrogen, halogen, alkyl, heteroalkyl, aryl, heteroaryl, carbocycle aliphatic ring and heterocycle aliphatic ring, amino or hydroxy; $R^2$ and $R^3$ are independently hydrogen, alkyl, heteroalkyl, aryl, aryl(akylene), heteroaryl, heteroaryl(alkylene), carbocycle, carbocycle(alkylene), heterocycle, and heterocycle(alkylene); each occurrence of $R^4$ is independently selected from halogen, alkyl, heteroalkyl, aryl, heteroaryl, carbocycle aliphatic ring and heterocycle aliphatic ring, amino or hydroxy; and n is 0, 1, 2 or 3.

In various aspects, the present invention provides compounds of structure (I) as defined above, however: n is 0; or n is 1; or $R^2$ is H; or n is 0 and $R^2$ is H; or n is 1 and $R^2$ is H.

In addition, in any of the above-described aspects, the present invention provides compounds wherein $R^1$ is $R^5$—$SO_2$— and $R^5$ is selected from alkyl, heteroalkyl, aryl, carbocycle, aryl(alkylene), and carbocycle(alkylene); or $R^1$ is $R^5$—$SO_2$— and $R^5$ is selected from alkyl, heteroalkyl, aryl, carbocycle, aryl(alkylene), and carbocycle(alkylene) where alkyl is $C_1$–$C_{10}$alkyl, heteroalkyl is $C_1$–$C_{10}$alkyl with 1, 2 or 3 heteroatoms selected from N, O and S, aryl is phenyl, substituted phenyl, naphthyl or substituted naphthyl, carbocycle is $C_3$–$C_8$carbocycle, and alkylene is $C_1$–$C_{10}$alkylene; or $R^1$ is $R^5$—$SO_2$— and $R^5$ is selected from alkyl, heteroalkyl, aryl, carbocycle, aryl(alkylene), and carbocycle(alkylene) such that $R^1$ is selected from $(C_1$–$C_6$alkyl)$SO_2$—, $PhSO_2$—, fluorinatedphenyl$SO_2$—, $PhCH_2SO_2$—, cyclopentyl$SO_2$—, m-carboxyphenyl$SO_2$—, m-methylphenyl$SO_2$—, and $HOOC$—$(C_1$–$C_4$alkylene)$SO_2$—.

In addition, in any of the above-described aspects, unless otherwise inconsistent therewith, the present invention provides compounds of structure (I) wherein $R^1$ is selected from halogen, amino, hydrocarbylamino, dihydrocarbylamino, hydrocarbyloxy, hydrocarbylthio, heterocyclyl, (heteroalkyl)amino, and (heteroaryl)amino; optionally, $R^1$ is selected from amino, $(C_1$–$C_6$alkyl)$(C_1$–$C_6$alkyl)amino, PhNH—, PhCH$_2$NH—,

and $HOCH_2CH_2NH$—; optionally, $R^1$ is selected from halide and $(C_1$–$C_6$alkyl)S—; optionally $R^1$ is chloride.

In addition, in any of the above-described aspects, unless otherwise inconsistent therewith, the present invention provides compounds of structure (I) wherein $R^3$ is selected from aryl, aryl(alkylene), heteroaryl, and heteroaryl(alkylene); optionally $R^3$ is aryl.

In another aspect, the present invention provides a compound having structure (II)

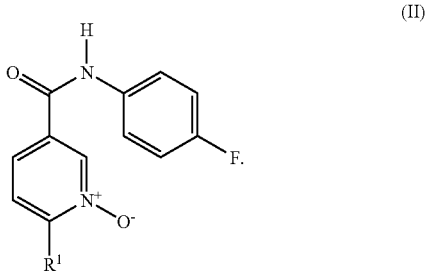

In addition, in any of the above-described aspects, unless otherwise inconsistent therewith, the present invention provides compounds of structure (I) wherein $R^3$ is benzyl or phenyl, the benzyl or phenyl having 0, 1, 2, 3 or 4 substituents selected from alkoxy, alkoxycarbonyl, alkyl, alkylamido, alkylcarbonyl, amido, benzyl optionally substituted with halogen, benzyloxy, carboxy, cyano, dialkylamido, haloalkyl, haloalkyloxy, halogen, hydroxy, nitro, oxoalkyl, phenyl optionally substituted with halogen, thioalkyl, thiocyanate, and thiohaloalkyl.

In addition, in any of the above-described aspects, unless otherwise inconsistent therewith, the present invention provides compounds of structure (I) wherein $R^3$ is selected from cycloalkyl, cycloalkyl(alkylene), cycloalkyl(heteroalkylene), heterocycloalkyl, heterocycloalkyl(alkylene), heterocycloalkyl(heteroalkylene), heteroaryl, heteroaryl(alkylene), and heteroaryl(heteroalkylene).

In addition, in any of the above-described aspects, unless otherwise inconsistent therewith, the present invention provides compounds of structure (I) wherein $R^1$ is selected from halogen, heteroalkyl or amino, $R^2$ is H, $R^3$ is aryl and $R^4$ is H.

In addition, the present invention provides each of the following compounds, either separately (i.e., in isolation) or in any combination: 6-chloro-N-(4-fluoro-phenyl)-1-oxy-nicotinamide; N-(4-fluoro-phenyl)-6-(2-hydroxy-ethylamino)-1-oxy-nicotinamide; 6-bromo-N-(4-fluoro-phenyl)-1-oxy-nicotinamide; 5,6-dichloro-N-(4-fluoro-phenyl)-1-oxy-nicotinamide; 6-ethanesulfonyl-N-(4-fluoro-phenyl)-1-oxy-nicotinamide; N-(4-fluorophenyl)-1-oxy-6-(propane-2-sulfonyl)-nicotinamide; N-(4-fluoro-phenyl)-6-methanesulfonyl-1-oxy-nicotinamide; 6-benzenesulfonyl-N-(4-fluoro-phenyl)-1-oxy-nicotinamide; N-(4-fluoro-phenyl)-1-oxy-6-phenylmethanesulfonyl-nicotinamide; 6-chloro-N-(3-chloro-4-fluoro-phenyl)-1-oxy-nicotinamide; and 6-chloro-N-(4-iodo-phenyl)-1-oxy-nicotinamide.

In another aspect, the present invention provides composition comprising a compound or compounds as set forth in any of the above-mentioned aspects, and a pharmaceutically acceptable carrier, adjuvant or excipient.

Furthermore, the present invention provides a method for antagonizing chemokine receptors comprising administering to a patient in need thereof an effective amount of a compound as set forth in any of the above-mentioned aspects.

The present invention also provides a method for inhibiting a chemokine-mediated cellular event comprising administering to a patient in need thereof an effective amount of a compound as set forth in any of the above-mentioned aspects. Optionally, the compounds inhibits a CXCR1 receptor; and/or inhibits a CXCR2 receptor.

The present invention additionally provides a method for the treatment of a disorder selected from Inflammatory Bowel Disease (IBD), psoriasis, rheumatoid arthritis, Acute Respiratory Distress Syndrome (ARDS), cancer, atherosclerosis, reperfusion injury, and graft vs. host disease.

In a further aspect, the present invention provides a method for inhibiting a G-protein-coupled, seven-transmembrane domain (7TM) receptor in a patient comprising administering to the patient a compound as set forth in any of the above-mentioned aspects in an amount effective to inhibit the receptor. Optionally, the compound modulates the binding of MIP-1β to a NPY cell receptor; and/or the compound modulates the binding of MIP-1β to a somatostatin cell receptor; and/or the compound modulates the binding of MIP-1β to a CCR5 cell receptor.

The present invention also provides a method for treating an inflammation event, comprising administering to a patient in need thereof, through a therapeutically or prophylactically acceptable manner, a therapeutically or pharmaceutically effective amount of a compound as set forth in any of the above-mentioned aspects. Optionally, the administration is selected from transdermal, oral, intravenous, intramuscular, vaginal, rectal, pulmonary, subcutaneous, sublingual and transmucosal administration.

Furthermore, the present invention provides a method for identifying a binding partner to a compound as set forth in any of the above-mentioned aspects comprising: immoblizing proteins known to be involved in the TNF-α signaling pathway onto a suitable carrier; and passing a solution of said compounds in isolation or mixture over said proteins and analyzing for compound:protein complex formation using surface plasmon resonance (SPR).

In another aspect, the present invention provides a method for identifying a binding partner to a compound as set forth in any of the above-mentioned aspects comprising: providing said compound(s) bound to a solid support to provide solid phase compounds; contacting a cell or cell components with said solid phase compounds in isolation or mixture; removing uncomplexed cellular material, for example by gentle washing with aqueous buffer; and recovering said binding partner from the solid phase compounds.

These and other related aspects of the present invention are set forth in more detail below.

DETAILED DESCRIPTION OF THE INVENTION

In one aspect, the present invention provides nicotinanilide-N-oxide compounds having the structure (I):

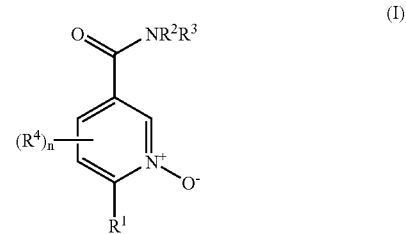

and optical isomers, diastereomers, enantiomers, solvates and pharmaceutically acceptable salts thereof, wherein $R^1$ is selected from $R^5$ and $R^5$—($C_1$–$C_6$heteroalkylene)- where $R^5$ is selected from hydrogen, halogen, alkyl, heteroalkyl, aryl, heteroaryl, carbocycle aliphatic ring and heterocycle aliphatic ring, amino or hydroxy; $R^2$ and $R^3$ are independently hydrogen, alkyl, heteroalkyl, aryl, aryl(akylene), heteroaryl, heteroaryl(alkylene), carbocycle, carbocycle(alkylene), heterocycle, and heterocycle(alkylene); each occurrence of $R^4$ is independently selected from halogen, alkyl, heteroalkyl, aryl, heteroaryl, carbocycle aliphatic ring and heterocycle aliphatic ring, amino or hydroxy; and n is 0, 1, 2 or 3. In addition, the present invention provides pharmaceutical compositions including said nicotinanilide-N-oxide compounds, and method of using said compounds and compositions, particularly in therapy.

Prior to setting forth a detailed description of the compounds, compositions and methods of the present invention, the following definitions as used herein are provided.

Definition of Terms

"Alkyl" is a saturated or unsaturated, straight or branched, hydrocarbon chain. In various embodiments, the alkyl group has 1–18 carbon atoms, i.e., is a C1–C18 group, or is a C1–C12 group, a C1–C6 group, or a C1–C4 group. Independently, in various embodiments, the alkyl group has zero branches (i.e., is a straight chain), one branch, two branches, or more than two branches. Independently, in one embodiment, the alkyl group is saturated. In another embodiment, the alkyl group is unsaturated. In various embodiments, the unsaturated alkyl may have one double bond, two double bonds, more than two double bonds, and/or one triple bond, two triple bonds, or more than two triple bonds. Exemplary alkyl groups include, without limitation, $CH_3$—, $CH_3CH_2$—, $CH_2$=CH—, $CH_3CH_2CH_2$—, $CH_2(CH_3)CH_2$—, $CH_3C(CH_3)_2CH_2$—. Alkyl chains may be substituted or unsubstituted. In one embodiment, the alkyl chains are unsubstituted. In another embodiment, the alkyl chain is substituted, e.g., with 1 substituent (i.e., the alkyl group is monosubstituted), or 1–2 substituents, or 1–3 substituents, or 1–4 substituents, etc. When substituted with a heteroatom, the substituted alkyl group may be referred to as a heteroalkyl.

"Alkylene" refers to a divalent alkyl radical, i.e., if hydrogen were to occupy one open valence site of an alkylene group then a alkyl group would result. Exemplary alkylene groups include, without limitation, —CH$_2$—, —CH$_2$CH$_2$—, —CH=CH—, —CH$_2$CH$_2$CH$_2$—, —CH(CH$_3$)CH$_2$—, —CH$_2$C(CH$_3$)$_2$CH$_2$—. As with alkyl groups, the alkylene group may be substituted or unsubstituted. In one embodiment, the alkylene group is unsubstituted. In another embodiment, the alkylene group is substituted, e.g., with 1 substituent (i.e., the alkylene group is monosubstituted), or 1–2 substituents, or 1–3 substituents, or 1–4 substituents, etc. When substituted with a heteroatom, the substituted alkylene group may optionally be referred to as a heteroalkylene. In one embodiment, the alkylene group is joined to an aryl group, so as to form an aryl(alkylene) group, also referred to as an aralkyl group. In one embodiment, aryl(alkylene) refers to C$_7$–C$_{20}$ groups, such as benzyl, α-methylbenzyl, α,α-dimethylbenzyl, phenylethyl (a.k.a. phenethyl), phenylpropyl, phenylbutyl and phenylhexyl are exemplary aralkyl groups. In another embodiment, the aralkyl group is C$_7$–C$_{11}$. In other embodiments, the alkylene group may be joined to a heteroaryl group (so as to form a heteroaryl(alkylene) group), a carbocycle group (so as to form a carbocycle(alkylene) group), and a heterocycle group (so as to form a heterocycle(alkylene) group).

"Aryl" is an aromatic hydrocarbon ring system. The ring system may be monocyclic or polycyclic (i.e., bicyclic, tricyclic, etc.). In various embodiments, the monocyclic aryl ring is C5–C10, or C5–C7, or C5–C6, where these carbon numbers refer to the number of carbon atoms that make up the ring system. A C6 ring system, i.e., phenyl, is a preferred aryl ring. In various embodiments, the polycyclic ring is a bicyclic aryl ring, where preferred bicyclic aryl rings are C8–C12, or C9–C10. A naphthyl ring, which has 10 carbon atoms, is a preferred polycyclic aryl ring. Aryl rings may be substituted or unsubstituted. In one embodiment, the aryl ring is unsubstituted. In another embodiment, the aryl ring is substituted with 1 substituent (i.e., the aryl ring is monosubstituted), or 1–2 substituents, or 1–3 substituents, or 1–4 substituents, etc.

"Carbocyclic aliphatic ring," also referred to as carbocycle or cycloalkyl, is a saturated or unsaturated, monocyclic or polycyclic (i.e., bicyclic, tricyclic, etc.) hydrocarbon ring. Carbocyclic aliphatic rings are not aromatic. A polycyclic hydrocarbon ring may include fused, spiro or bridged ring structures. In various embodiments, the monocyclic carbocyclic aliphatic ring is a C3–C10, or a C4–C7, or a C5–C6 ring system. In various embodiments, the polycyclic carbocyclic aliphatic ring is a C6–C12, or a C9–C10 ring system. In one embodiment, the polycyclic ring is bicyclic. In another embodiment, the polycyclic ring is bicyclic or tricyclic. Carbocyclic aliphatic rings include cyclopropylcyclopentyl, cyclohexyl, cyclohexenyl, cycloheptyl, and cyclooctyl. Carbocycles may be substituted or unsubstituted. In one embodiment, the carbocycle is unsubstituted. In another embodiment, the carbocycle is substituted with, e.g., 1 substituent (i.e., the alkyl group is monosubstituted), or 1–2 substituents, or 1–3 substituents, or 1–4 substituents, etc.

"Haloalkyl" is an alkyl chain substituted with one or more halogens. A preferred haloalkyl is trifluoromethyl.

"Halogen" refers to fluoride, chloride, bromide or iodide. In a preferred embodiment, halogen refers to fluoride or chloride.

"Heteroalkyl" is a monovalent, saturated or unsaturated, straight or branched, chain containing carbon and at least one heteroatom. The heteroalkyl group may, in various embodiments, have one heteroatom, or 1–2 heteroatoms, or 1–3 heteroatoms, or 1–4 heteroatoms. Heteroalkyl chains may contain from 1 to 18 (i.e., 1–18) member atoms (carbon and heteroatoms) in the chain, and in various embodiments contain 1–12, or 1–6, or 1–4 member atoms. Independently, in various embodiments, the heteroalkyl group has zero branches (i.e., is a straight chain), one branch, two branches, or more than two branches. Independently, in one embodiment, the heteroalkyl group is saturated. In another embodiment, the heteroalkyl group is unsaturated. In various embodiments, the unsaturated heteroalkyl may have one double bond, two double bonds, more than two double bonds, and/or one triple bond, two triple bonds, or more than two triple bonds. Heteroalkyl chains may be substituted or unsubstituted. In one embodiment, the heteroalkyl chain is unsubstituted. In another embodiment, the heteroalkyl chain is substituted. A substituted heteroalkyl chain may have 1 substituent (i. e., be monosubstituted), or may have 1–2 substituents, or 1–3 substituents, or 1–4 substituents, etc.

"Heteroalkylene" refers to an alkylene group wherein one or more of the carbons is replaced with a heteroatom. Thus, the heteroalkylene group is a saturated or unsaturated, straight or branched chain divalent radical that contains at least one heteroatom. The heteroalkylene group may, in various embodiments, have one heteroatom, or 1–2 heteroatoms, or 1–3 heteroatoms, or 1–4 heteroatoms. Heteroalkylene chains may contain from 1 to 18 (i.e., 1–18) member atoms (carbons and/or heteroatoms) in the chain, and in various embodiments contain 1–12, or 1–6, or 1–4 member atoms. Independently, in various embodiments, the heteroalkylene group has zero branches (i.e., is a straight chain), one branch, two branches, or more than two branches. Independently, in one embodiment, the heteroalkylene group is saturated. In another embodiment, the heteroalkylene group is unsaturated. In various embodiments, the unsaturated heteroalkylene may have one double bond, two double bonds, more than two double bonds, and/or one triple bond, two triple bonds, or more than two triple bonds.

"Heteroaryl" is an aromatic ring system containing carbon and at least one heteroatom, that is, the heteroaryl group includes at least one aromatic ring containing a heteroatom, i.e., a heteroaryl ring. The heteroaryl ring may, in various embodiments, have 1 heteroatom, 1–2 heteroatoms, 1–3 heteroatoms, or 1–4 heteroatoms in the heteroaryl ring. Heteroaryl groups may be monocyclic or polycyclic (i.e., bicyclic, tricyclic, etc.), where the polycyclic ring may contained fused, spiro or bridged ring junctions. In one embodiment, the heteroaryl is monocyclic, while in another embodiment the heteroaryl group is selected from monocyclic and bicyclic rings. Monocyclic heteroaryl rings may contain from about 5 to about 10 member atoms (carbon and heteroatoms), preferably from 5–7, and most preferably from 5–6 member atoms in the ring. Bicyclic heteroaryl groups may contain from about 8–12 member atoms, or 9–10 member atoms in the rings. In a polycyclic heteroaryl group, at least one ring contains heteroatoms, and the heteroatom-containing ring is aromatic. The additional rings may or may not, independently in each ring, contain heteroatom(s). If an additional ring contains heteroatom(s), then in various embodiments an additional ring has 1 heteroatom, 1–2 heteroatoms, or 1–3 heteroatoms. Independently, the additional rings may or may not be aromatic, that is, they may be saturated, unsaturated but not aromatic, or aromatic. The heteroaryl group may be unsubstituted or substituted. In one embodiment, the heteroaryl group is unsubstituted. In another embodiment, the heteroaryl group is substituted. The substituted heteroaryl group may, in various embodiments, contain 1 substituent, 1–2 substituents, 1–3 substituents, or 1–4 substituents. Exemplary heteroaryl groups include, without limitation, benzofuran, benzothiophene, furan, imidazole, indole, isothiazole, oxazole, pyrazine, pyrazole, pyridazine, pyridine, pyrimidine, pyrrole, quinoline, thiazole and thiophene.

"Heteroatom" is a nitrogen, sulfur, or oxygen atom. Groups containing more than one heteroatom may contain different heteroatoms, i.e., heteroatoms are selected on an independent basis upon each occurrence.

"Heterocyclic aliphatic ring," also referred to as heterocyclyl or cycloheteroalkyl or heterocycloalkyl, is a saturated or unsaturated, monocyclic or polycyclic (i.e., bicyclic, tricyclic, etc.) ring containing carbon and at least one heteroatom. Heterocyclic aliphatic rings are not aromatic. The heterocyclic aliphatic ring may, in various embodiments, have one heteroatom, or 1–2 heteroatoms, or 1–3 heteroatoms, or 1–4 heteroatoms, etc. In one embodiment, the heterocyclic aliphatic ring is monocyclic, where the monocyclic ring may have 3–10, or 4–7, or 5–6 member atoms. In another embodiment, the heterocyclic aliphatic ring is polycyclic, where in various embodiments, the ring may be bicyclic, or may be tricyclic, or may be either bicyclic or tricyclic. A polycyclic ring system may have one or more fused, spiro or bridged ring systems. The polycyclic heterocyclic aliphatic ring system may have 6–12, or 9–10 member atoms. The heterocyclic ring may be unsubstituted or substituted. In one embodiment, the heterocyclic ring is unsubstituted. In another embodiment, the heterocyclic ring is substituted. The substituted heterocyclic ring may contain 1 substituent, or 1–2 substituents, or 1–3 substituents, or 1–4 substituents, etc. Exemplary heterocyclic aliphatic rings include piperazyl, morpholinyl, tetrahydrofuranyl, tetrahydropyranyl and piperidyl.

"Lower alkyl" is an alkyl chain comprised of 1–6, preferably 1–4 carbon atoms.

"Pharmaceutically acceptable salt" and "salts thereof" means organic or inorganic salts of the pharmaceutically important molecule. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically important organic molecule may have more than one charged atom in its structure. Situations where multiple charged atoms are part of the molecule may have multiple counterions. Hence, the molecule of a pharmaceutically acceptable salt may contain one or more than one charged atoms and may also contain, one or more than one counterion. The desired charge distribution is determined according to methods of drug administration. Examples of pharmaceutically acceptable salts are well known in the art but, without limiting the scope of the present invention, exemplary presentations can be found in the Physician's Desk Reference, The Merck Index, The Pharmacopoeia and Goodman & Gilman's The Pharmacological Basis of Therapeutics.

"Substituents" replace a hydrogen atom with a non-hydrogen atom on an alkyl, heteroalkyl, aryl, heteroaryl, carbocycle, and/or heterocyclyl group as defined herein. Where the substituent contains a heteroatom, that heteroatom may be at any acceptable oxidation state for that particular atom, e.g., sulfur as part of a substituent may vary from an oxidation state of −2 to +8, and may be part of a complex or chelate as in a sulfoxide a mercapto-phosphine or metal chelated in a thia-crown ether. Suitable substituents that may be located on one or more of these groups include the following: alkoxy (i.e., alkyl-O—, e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, alkyloxycarbonyloxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonylphenylthio), amino (e.g., amino, mono- and di- C1–C3 alkanylamino, methylphenylamino, methylbenzylamino, C1–C3 alkanylamido, acylamino, carbamamido, ureido, guanidino, nitro and cyano). Moreover, any substituent may have from 1–5 further substituents attached thereto.

"Amino" means a trivalent amine substituted with up to 2 alkyl groups as defined above or with 1 alkyl group and a hydrogen group, or with one aryl and one alkyl groups, or with two aryl groups, or with two or more hydrogen groups or with the substitution required to complete the nitrogen's valence requirements. "Amino" further includes amino salts where the nitrogen is hypervalent, having four bonds and may or may not have a charge and a counterion. The counterion, when present, may be an external inorganic and/or organic counterion and/or may be an internal counterion. Inorganic counterions include, for example, anions such as halo anions and other non-metal anions. Examples of organic counterions include, for example, anionic organic moieties such as acetate, citrate and other anionic organic moieties.

As stated previously, the present invention provides nicotinanilide-N-oxide compounds having the structure (I):

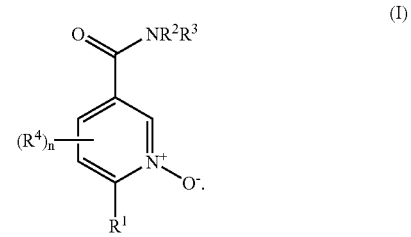

The inventive compounds include optical isomers, diastereomers, enantiomers, solvates and pharmaceutically acceptable salts including the structure (I). The structure (I) does not show an optically active center. Accordingly, the optical isomers of the present invention have an optically active center in one or more of $R^1$, $R^2$, $R^3$ and $R^4$. When an optically active center is present in an inventive compound, the invention provides for mixtures of optically active compounds as well as isolated optically active compounds. An optically active compound may be isolated by, for example, chiral resolution techniques. Likewise, the presence of diastereomeric and enantiomeric forms of the compounds of structure (I) depend on the identities of $R^1$, $R^2$, $R^3$ and $R^4$. Again, when the compounds of the invention may be present in diastereomerically pure or mixed form, or enantiomerically pure or mixed form, the present invention provides for both mixtures and isolated compounds.

Pharmaceutically acceptable salts of the compounds of structure (I) may be formed, depending on whether one or more of $R^1$, $R^2$, $R^3$ and $R^4$ contain an acidic or basic site. Suitable counterions for the pharmaceutically acceptable salts include chloride, sulfate, phosphate, citrate, fumarate, methanesulfonate, acetate, tartrate, maleate, lactate, mandelate, salicylate, succinate and other salts known in the art.

The value of n in the compounds of the invention may be 0, 1, 2 or 3. In one aspect of the invention n is 0, such that the anilide ring contains three hydrogen substituents in addition to $R^1$. In another aspect, n is 1 such that the anilide rings contains 2 hydrogen substituents. In another aspect, n is 2 such that the anilide rings contains 1 hydrogen substituents. In another aspect, n is selected from 0 and 1. In another aspect, n is selected from 0, 1 and 2. In another aspect, n is selected from 1 and 2.

The identity of $R^1$ is selected from $R^5$ and $R^5$—($C_1$–$C_6$heteroalkylene)- where $R^5$, is, selected from hydrogen, halogen, alkyl, heteroalkyl, aryl, heteroaryl, carbocycle aliphatic ring, heterocycle aliphatic ring, amino and hydroxy. In one aspect, $R^1$ is $R^5$ and does not include $R^5$—($C_1$–$C_6$heteroalkylene)-. In another aspect, $R^1$ is $R^5$—($C_1$–$C_6$heteroalkylene)- and does not include $R^5$ alone.

In another aspect, $R^1$ is $R^5$—$SO_2$— (i.e., $R^1$ is $R^5$—($C_1$–$C_6$heteroalkylene)- where ($C_1$–$C_6$heteroalkylene) is $SO_2$) and $R^5$ is selected from alkyl, heteroalkyl, aryl, carbocycle, aryl(alkylene), and carbocycle(alkylene). In various aspects, alkyl refers to $C_1$–$C_{10}$alkyl; heteroalkyl refers to $C_1$–$C_{10}$alkyl with 1, 2 or 3 heteroatoms selected from N, O and S; aryl refers to phenyl, substituted phenyl, naphthyl or substituted naphthyl; carbocycle refers to $C_3$–$C_8$carbocycle; and alkylene refers to $C_1$–$C_{10}$alkylene. In various other aspects, $R^1$ is selected from ($C_1$–$C_6$alkyl)$SO_2$—, $PhSO_2$—, fluorinatedphenyl$SO_2$—, $PhCH_2SO_2$—, cyclopentyl$SO_2$—, m-carboxyphenyl$SO_2$—, m-methylphenyl$SO_2$—, and $HOOC$—($C_1$–$C_4$alkylene)$SO_2$—.

In another aspect, $R^1$ is selected from halogen, amino, hydrocarbylamino, dihydrocarbylamino, hydrocarbyloxy, hydrocarbylthio, heterocyclyl, (heteroalkyl)amino, and (heteroaryl)amino. In various aspects, $R^1$ is selected from amino, ($C_1$–$C_6$alkyl)($C_1$–$C_6$alkyl)amino, PhNH—, $PhCH_2NH$—,

and $HOCH_2CH_2NH$—. In yet other aspects $R^1$ is selected from halide and ($C_1$–$C_6$alkyl)S—, where $R^1$ may be, in one aspect, chloride.

The compounds of the invention have amide substitution on the anilide ring, and in particular have a —C(=O)$NR^2R^3$ substituent on the anilide ring. The $R^2$ and $R^3$ groups are independently selected from hydrogen, alkyl, heteroalkyl, aryl, aryl(akylene), heteroaryl, heteroaryl(alkylene), carbocycle, carbocycle(alkylene), heterocycle, and heterocycle (alkylene). In one aspect, $R^2$ is hydrogen. In another aspect, $R^2$ is hydrogen when n is 0. In another aspect, $R^2$ is hydrogen when n is 1.

In various aspects, and optionally in addition to the other particular aspects defined above, the compounds of the invention have $R^3$ selected from aryl, aryl(alkylene), heteroaryl, and heteroaryl(alkylene). In one aspect, $R^3$ is aryl. In another aspect, $R^3$ is para-fluorophenyl. In another aspect, $R^2$ is hydrogen, n is zero, and $R^3$ is para-fluorophenyl, so that the invention provides compounds having structure (II):

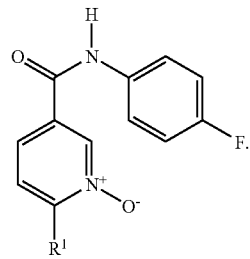

In another aspect, the present invention provides compounds of structure (I) wherein $R^3$ is benzyl or phenyl, the benzyl or phenyl having 0, 1, 2, 3 or 4 substituents selected from alkoxy, alkoxycarbonyl, alkyl, alkylamido, alkylcarbonyl, amido, benzyl optionally substituted with halogen, benzyloxy, carboxy, cyano, dialkylamido, haloalkyl, haloalkyloxy, halogen, hydroxy, nitro, oxoalkyl, phenyl optionally substituted with halogen, thioalkyl, thiocyanate, and thiohaloalkyl, where in a preferred aspect $R^2$ is defined as hydrogen.

In another aspect, the present invention provides compound of structure (I) wherein $R^3$ is selected from cycloalkyl, cycloalkyl(alkylene), cycloalkyl(heteroalkylene), heterocycloalkyl, heterocycloalkyl(alkylene), heterocycloalkyl(heteroalkylene), heteroaryl, heteroaryl(alkylene), and heteroaryl(heteroalkylene), where in a preferred aspect $R^2$ is defined as hydrogen.

In compounds of the invention, $R^4$ is independently selected from halogen, alkyl, heteroalkyl, aryl, heteroaryl, carbocycle aliphatic ring and heterocycle aliphatic ring, amino and hydroxy. In one aspect, $R^4$ is independently selected from halogen, alkyl, heteroalkyl, amino and hydroxy. In one aspect, $R^4$ is selected from halogen and alkyl.

Nicotinanilide-N-oxides of the present invention may be prepared as depicted in Scheme 1. The starting material 1 in Scheme 1 is an activated nicotinic acid, where Y is a suitable carbonyl-activating group such as halogen, 1-hydroxybenzotriazole, 7-aza-1-hydroxybenzotriazole, or other leaving group capable of being displaced by an amine. Also in 1, n is 0, 1, 2 or 3, and $R^1$ is either $R^1$ or a synthetic precursor to $R^1$, where $R^1$ is selected from $R^5$ and $R^5$—($C_1$–$C_6$heteroalkylene)- and $R^5$ is selected from hydrogen, halogen, alkyl, heteroalkyl, aryl, heteroaryl, carbocycle aliphatic ring and heterocycle aliphatic ring, amino or hydroxy. In 1, each occurrence of $R^4$ is independently selected from halogen, alkyl, heteroalkyl, aryl, heteroaryl, carbocycle aliphatic ring and heterocycle aliphatic ring, amino or hydroxy; or is a suitable synthetic precursor to a listed $R^4$ group.

Compounds of formula 1 are either commercially available from standard chemical supply houses, or may be readily prepared from the corresponding commercially available nicotinic acids upon treatment with an activating agent, e.g., thionyl chloride. Alternatively, they may be prepared by methodology known to one of skill in the art, based on information in the chemical and patent literature, and compounds known in the literature. See, e.g., Arch. Pharm. (Weinheim Ger.) 290:20–25, 1957; J. Fluorine Chemistry, 101(1):45–60, 2000; J. Chem. Soc. 5045–5048, 1965; J. Chem. Soc. 73:234, 1898; J. Med. Chem. 35(3): 518–525, 1992; U.S. Pat. Nos. 3,950,160, 3,766,195 and 3,637,716; German Patent DE 25 38 950, and Great Britain Patent GB 1,134,651.

Commercially available chemicals may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury CN), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Compounds described in the chemical literature as referred to herein may be identified though various reference books and databases. Suitable reference books and treatise that detail the synthesis of reactants useful in the preparation of compounds of the present invention, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modem Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942–2000) John Wiley & Sons, in over 55 volumes; and "Chemistry of Functional Groups" John Wiley & Sons, in 73 volumes. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., www.acs.org may be contacted for more details). Chemicals that are known but not commercially available in catalogs may be prepared by custom chemical synthesis houses, where many of the standard chemical supply houses (e.g., those listed above) provide custom synthesis services.

Scheme 1

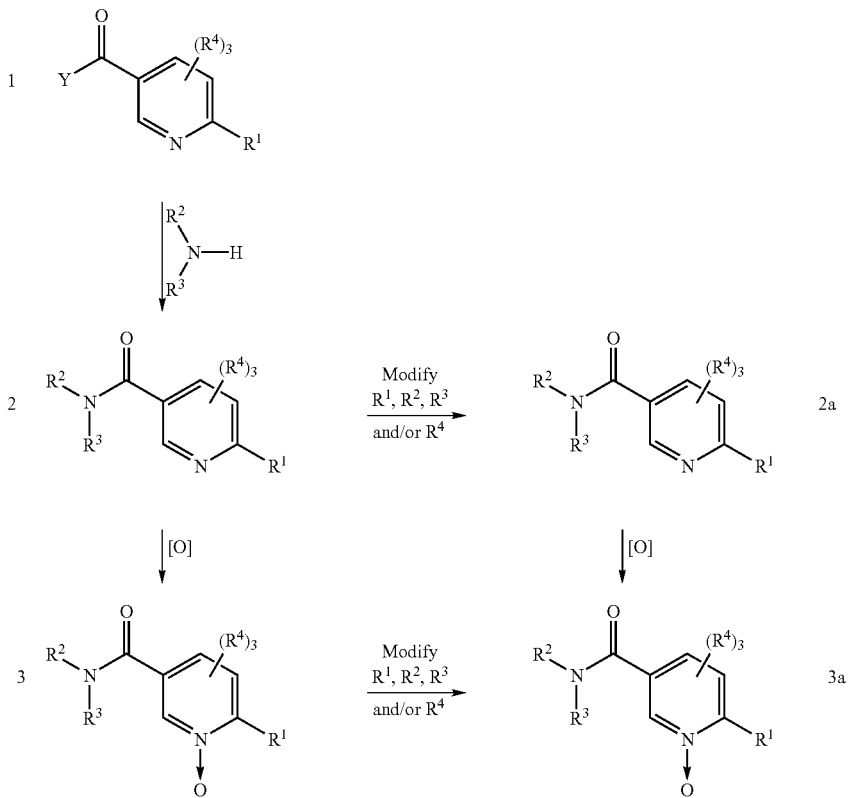

As shown in Scheme 1, the nicotinic acid derivative 1 couples with a primary or secondary amine (HNR²R³) to provide an amide intermediate 2. The coupling reaction is typically carried out in a suitable solvent, e.g., dichloromethane (DCM), in the presence of a suitable base, e.g. a tertiary amine such as diisopropylethylamine (DIEA), at a suitable reaction temperature, e.g., room temperature (rt).

In amines of the formula HNR²R³, R² and R³ are independently selected from hydrogen, alkyl, heteroalkyl, aryl, aryl(akylene), heteroaryl, heteroaryl(alkylene), carbocycle, carbocycle(alkylene), heterocycle, and heterocycle(alkylene). Many such amines are available from chemical supply houses, or may be prepared by methodology well known in the chemical literature.

The intermediate 2 may be oxidized under suitable conditions to give the nicotinanilide N-oxide 3. For example, 2 may be reacted with a suitable oxidizing reagent, e.g., aqueous hydrogen peroxide, in a suitable solvent such as acetic acid or trifluoroacetic acid at a suitable reaction temperature, e.g., between about rt and about 70° C. If desired, the nicotinanilide N-oxide 3 may be reacted under suitable reaction conditions to change any one or more of R¹, R², R³ and R⁴ and so form nicotinanilide N-oxide 3a, where R¹, R², R³ and R⁴ in 3a are as defined above.

Alternatively, the intermediate 2 may be reacted under suitable reaction conditions to change any one or more of R¹, R², R³ and R⁴ and so provide the intermediate 2a. This intermediate 2a may then be exposed to oxidizing reaction conditions to form nicotinanilide N-oxide 3a. In each of 2 and 2a, R¹, R², R³ and R⁴ are as defined above.

For example, when R¹ in intermediate 2 is a leaving group, e.g., halide, the intermediate 2 may be treated with a nucleophile that replaces the halide with another R¹ group. Suitable conditions for this type of transformation involve performing the reaction in a suitable solvent, e.g., tetrahydrofuran (THF), at a temperature, e.g., between room temperature and about 90° C., and optionally under pressure, e.g., a sealed tube. Suitable nucleophiles include, but are not limited to, organoamines (e.g., dimethylamine, benzylamine, imidazole), alkoxides (e.g., sodium methoxide) and thiolates (e.g., sodium thiomethoxide).

The oxidizing conditions that convert 2 to 3, or 2a to 3a, may simultaneously oxidize one or more of the R¹, R², R³ and R⁴ groups. For instance, when R¹ is —NR⁵R⁶ or —SR⁵, the resulting intermediate may be oxidized under the same conditions as above to give the 6-N-oxide or the 6-sulfone, respectively.

Scheme 2 illustrates another route to nicotinanilide N-oxides 3.

Scheme 2

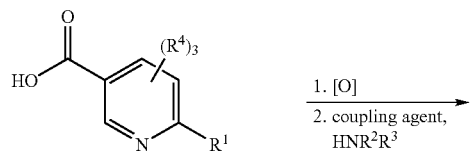

-continued

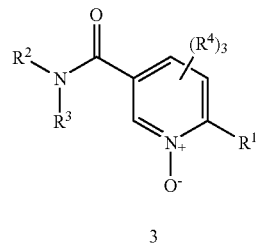

As shown in Scheme 2, nicotinic acid 4 is oxidized under suitable conditions as described above (e.g., with hydrogen peroxide), followed by coupling to a primary or secondary amine, HNR²R³. Suitable conditions for this type of coupling involve performing the reaction in a suitable solvent, e.g. THF, in the presence of a suitable coupling agent, e.g. 2-ethoxy-1-ethoxycarbonyl-1,2-dihydroquinoline (EEDQ), and if necessary, a suitable tertiary amine such as DIEA. Nicotinic acids 4 are commercially available or may be readily prepared from commercially available nicotinic acids.

C. Pharmaceutical Compositions

In another aspect, the present invention provides a composition containing a nicotinanilide N-oxide compound of formula (I) in admixture with a pharmaceutically acceptable adjuvant, carrier, diluent or excipient, i.e., the present invention provides a pharmaceutical composition containing a compound of formula (I). The pharmaceutical composition may contain optional ingredient(s) if desired.

The pharmaceutical compositions of the present invention may be in any form which allows for the composition to be administered to a patient. Typical routes of administration include, without limitation, oral, topical, parenteral, sublingual, rectal, vaginal, and intranasal. The term parenteral as used herein includes subcutaneous injections, intravenous, intramuscular, intrasternal injection or infusion techniques. Pharmaceutical composition of the invention are formulated so as to allow the active ingredients contained therein to be bioavailable upon administration of the composition to a patient. Compositions that will be administered to a patient take the form of one or more dosage units, where for example, a tablet may be a single dosage unit, and a container of nicotinanilide N-oxide in aerosol form may hold a plurality of dosage units.

The composition may be in the form of a solid, liquid or gas (aerosol). In one aspect, the carrier(s) are particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, chewing gum, wafer or the like form. Such a solid composition will typically contain one or more inert diluents or edible carriers. In addition, one or more of the following adjuvants may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol or a fatty oil.

The composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid compositions intended for either parenteral or oral administration should contain an amount of the inventive compound such that a suitable dosage will be obtained. Typically, this amount is at least 0.01% of a compound of the invention in the composition. When intended for oral administration, this amount may be varied to be between 0.1 and about 70% of the weight of the composition. Preferred oral compositions contain between about 4% and about 50% of the active vanadium(V) complex. Preferred compositions and preparations according to the present invention are prepared so that a parenteral dosage unit contains between 0.01 to 1% by weight of active compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the inventive compound of from about 0.1 to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule.

The composition in solid or liquid form may include an agent which binds to the nicotinanilide N-oxide compounds of the invention and thereby assists in the delivery of the active compound. Suitable agents which may act in this capacity include a monoclonal or polyclonal antibody, a protein or a liposome.

Materials used in preparing the pharmaceutical compositions should be pharmaceutically pure and non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. Preferred aerosols may be determined by one skilled in the art, without undue experimentation.

Whether in solid, liquid or gaseous form, the pharmaceutical composition of the present invention may contain one or more known pharmacological agents used in the treatment of inflammation.

The pharmaceutical compositions may be prepared by methodology well known in the pharmaceutical art. For example, a composition intended to be administered by injection can be prepared by combining a nicotinanilide N-oxide compounds of formula (I) with water so as to form a solution. A surfactant may be added to facilitate the formation of a homogeneous solution or suspension. Surfactants are compounds that non-covalently interact with the nicotinanilide N-oxide compound so as to facilitate dissolution or homogeneous suspension of the compound in the aqueous delivery system.

D. Biological Applications

The present invention provides nicotinanilide N-oxide, compositions containing a nicotinanilide N-oxide, and methods of using nicotinanilide N-oxide compounds to inhibit chemokine-mediated cellular events involving IL-8, including IL-8a (CXCR1 receptor) and IL-8b (CXCR2 receptor). Thus, in one aspect, the present invention provides a method to modulate binding of IL-8 to cell receptors, and/or modulate the consequential intracellular events comprising administering to a subject in a need thereof an effective amount of a nicotinanilide N-oxide compounds of formula (I). Thus, in one aspect, the present invention provides a method for the inhibition of IL-8 or other CXC chemokines binding to CXCR1 and/or CXCR2 receptors comprising administering an effective amount of a compound of formula (I) to a subject in need thereof. In another aspect, the present invention provides a method for reducing the levels of IL-8 within a subject comprising administering to a subject in need thereof an effective amount of a compound of formula (I). In another aspect, the present invention provides a method for treating, preventing, or treating and/or preventing one or more of inflammatory and autoimmune diseases such as Inflammatory Bowel Disease (IBD), psoriasis, rheumatoid arthritis, Acute Respiratory Distress Syndrome (ARDS), cancer, atherosclerosis, reperfusion injury, and graft vs. host disease, comprising administering to a subject in need thereof an effective amount of a compound of formula (I).

In another aspect, the present invention provides a method of using nicotinanilide N-oxide compounds, and compositions comprising nicotinanilide N-oxide compounds, to inhibit G-protein-coupled, seven-transmembrane domain (7TM) receptors. Thus, in one aspect, the present invention provides a method to modulate the binding of MIP-1β to CCR5 cell receptors. In another aspect, the present invention provides a method to modulate the binding of Peptide YY (PYY) to NPY cell receptors. In another aspect, the present invention provides a method to modulate the binding of somatostatin to somatostatin cell receptors. In one aspect, the nicotinanilide N-oxide compound modulates by reducing the effective binding of MIP-1β to cell receptor.

The present invention provides a method for treating an inflammation event, comprising administering to a patient in need thereof, through a therapeutically or prophylactically acceptable manner, a therapeutically or pharmaceutically effective amount of the compound of formula (I). Administering may be selected from transdermal, oral, intravenous, intramuscular, vaginal, rectal, pulmonary, subcutaneous, sublingual and transmucosal administration.

The "effective amount" or "therapeutically effective amount" of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

In another aspect, the present invention provides a method for identifying a binding partner to a nicotinanilide-N-oxide compound as disclosed herein, where the method comprises: immoblizing protein known to be involved in the TNF-α signaling pathway onto a suitable carrier; and passing a solution of said compounds in isolation or mixture over said protein and analyzing for compound:protein complex formation using surface plasmon resonance (SPR). This method may be performed in analogy to the method described in Karlsson, R et al. "Biosensor Analysis of Drug-Target Interactions: Direct and Competitive Binding Assays for Investigation of Interactions Between Thrombin and Thrombin Inhibitors" *Anal. Biochem.* 2000, 278(1), 1–13. For other examples of identifying small molecule-protein interactions using SPR see the Biacore website: http://www.biacore.com.

In another aspect, the present invention provides a method for identifying a binding partner to a nicotinanilide N-oxide compound as disclosed herein, where the method comprises: contacting a cell or cell components with said nicotinanilide N-oxide compound in isolation or mixture; removing uncomplexed cellular material, for example by gentle washing with aqueous buffer; and recovering said binding partner from the compounds. The nicotinanilide N-oxide compound(s) are preferably bound to a solid support See, e.g., methodology reported in Shimizu, N et al. "High Performance Affinity Beads for Identifying Drug Receptors" *Nature Biotechnology*, 2000, 18(8), 877–881).

As to each publication or patent referenced herein, that publication or patent is incorporated herein by reference in its entirety for all purposes.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The following examples are offered by way of illustration, and not by way of limitation.

EXAMPLES

Example 1

Synthesis of 6-Dimethylamino-N-(4-fluoro-phenyl)-1-oxy-nicotinamide

A. 6-Chloro-N-(4-fluoro-phenyl)-nicotinamide

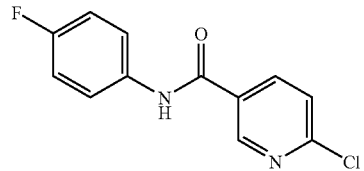

To a suspension of 6-chloronicotinoyl chloride (10.5 g, 59.7 mmole) in dry dichloromethane (100 mL) was added 4-fluoroaniline (5.6 mL, 59.7 mmole), followed by the dropwise addition of N,N-diisopropylethylamine (21 mL, 119 mmol). After stirring for 90 min at room temperature, the mixture was diluted with ethyl acetate (20 mL) and washed with water. The combined organic extracts were dried over anhydrous sodium sulfate, filtered, and concentrated in vacuo. Purification by recrystallization using ethyl acetate/hexanes gave 13.8 g (92%) of a white solid. $^1$H NMR (300 MHz, CDCl$_3$) δ7.09–7.12 (m, 2H), 7.47–7.50 (m, 1H), 7.56–60 (m, 2 H), 7.7 (bs, 1H), 8.15–8.18 (m, 1H), 8.84 (m, 1H); MS (EI) m/z 251.13 (M+H)$^+$.

B. 6-Chloro-N-(4-fluoro-phenyl)-1-oxy-nicotinamide

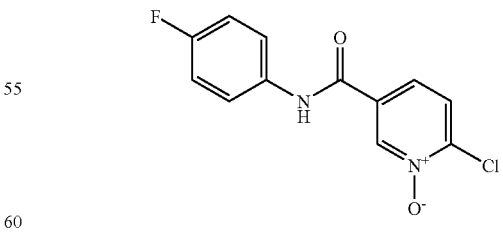

To a solution of 6-chloro-N-(4-fluoro-phenyl)-nicotinamide (2.06 g, 8.2 mmole) in 30 mL of acetic acid was added 30 mL of aqueous hydrogen peroxide (30%). The mixture was warmed to 70° C. and stirred for 18 hours, and then 20 mL of additional hydrogen peroxide (30%) was added and stirred for 2 hours. The mixture was then cooled, concentrated in vacuo and diluted with water (100 mL). Isolation of the precipitate by vacuum filtration afforded 0.43 g (20%) of the desired product as a white solid: ¹H NMR (300 MHz, DMSO-d₆) δ7.19 (m 2H), 7.75 (M, 3H), 7.95 (M, 1H), 8.94 (d, 1H, J=2.2 Hz), 10.5 (s, 1H); MS (EI) m/z 267.19 (M+H)⁺.

C. 6-Dimethylamino-N-(4-fluoro-phenyl)-1-oxy-nicotinamide

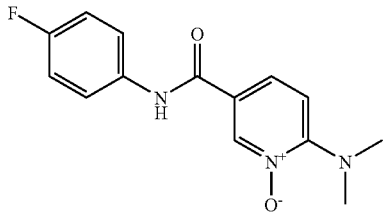

In a sealed tube was placed 6-chloro-N-(4-fluoro-phenyl)-1-oxy-nicotinamide (0.016 g, 0.060 mmole) and dimethylamine (2 mL of a of 2.0 M solution in THF). The mixture was heated to 90° C. for 4 h, then cooled and poured into ethyl acetate and water. The organic layer was removed, dried over sodium sulfate, filtered, and the solvents removed in vacuo. Purification by trituration using ethyl acetate/hexanes gave 6 mg (36%) of the desired product as a white solid: ¹H NMR (300 MHz, DMSO-d₆) δ3.00 (m, 6H), 7.10 (m, 3H), 7.7 (m, 3H), 8.68 (m, 1H), 10.26 (m, 1H); MS (EI) m/z 276.27 (M+H)⁺.

Example 2

Synthesis of 6-Benzylamino-N-(4-fluoro-phenyl)-1-oxy-nicotimamide

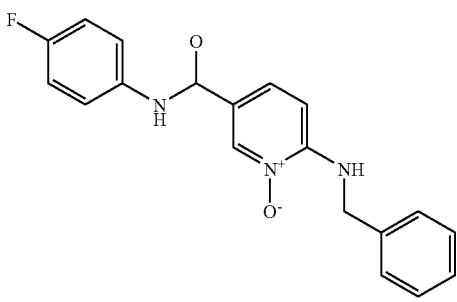

In a sealed tube was placed 6-chloro-N-(4-fluoro-phenyl)-1-oxy-nicotinamide (0.020 g, 0.070 mmole) and benzylamine (1 mL). The mixture was heated to 90° C. for 18 h, then cooled and poured into ether. The resulting precipitate was collected by vacuum filtration and purified by trituration with methanol/ethyl acetate to give 16 mg (70%) of the desired product as a white solid. ¹H NMR (300 MHz, CD₃OD) δ4.60 (m, 2H), 6.85 (m, 1H), 7.05 (m, 3H), 7.33 (m, 4H), 7.63 (m, 3H), 7.87 (m, 1H), 8.73 (s, 1H); MS (EI) m/z 338.26 (M+H)⁺.

Example 3

Synthesis of N-(4-Fluoro-phenyl)-1-oxy-6-phenylamino-nicotinamide

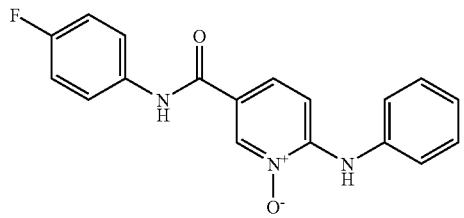

In a sealed tube was placed 6-chloro-N-(4-fluoro-phenyl)-1-oxy-nicotinamide (0.020 g, 0.070 mmole) and aniline (1 mL). The mixture was heated to 90° C. for 18 h then cooled and poured into ether. The resulting precipitate was collected by vacuum filtration and purified by trituration with ethyl acetate to give 13.1 mg (59%) of the desired product as a white solid. ¹H NMR (300 MHz, DMSO-₆) δ7.17 (m, 5H), 7.35 (m, 4H), 7.75 (m, 2H), 8.92 (d, 1H, J=2.2 Hz), 9.75 (s, 1H), 10.24 (s, 1H); MS (EI) m/z 322.23 (M−H)⁻.

Example 4

Synthesis of N-(4-Fluoro-phenyl)-6-methylamino-1-oxy-nicotinamide

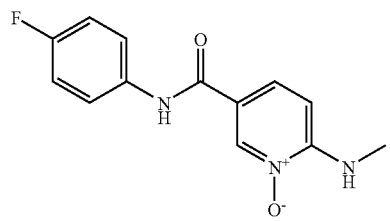

In a sealed tube was placed 6-chloro-N-(4-fluoro-phenyl)-1-oxy-nicotinamide (0.020 g, 0.070 mmole) and methylamine (1 mL of a 2.0 M solution in water). The mixture was heated to 90° C. for 18 h, then cooled and poured into ether. The resulting precipitate was collected by vacuum filtration and purified by flash chromatography (10% methanol in ammonia saturated dichloromethane) to give 5.6 mg (21%) of the desired product as a white solid. ¹H NMR (300 MHz, CD₃OD) δ3.05 (s, 3H), 6.94 (m, 1H), 7.06 (m, 2H), 7.64 (m, 2H), 8.00 (m, 1H), 8.70 (m, 1H); MS (EI) m/z 260.26 (M−H)⁻.

Example 5

Synthesis of N-(4-Fluoro-phenyl)-6-imidazol-1-yl-1-oxy-nicotinamide

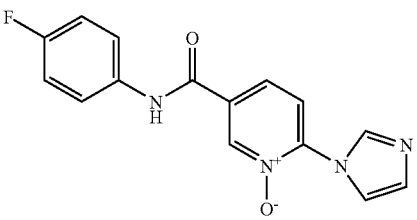

In a sealed tube was placed 6-chloro-N-(4-fluoro-phenyl)-1-oxy-nicotinamide (0.020 g, 0.070 mmole), imidazole (95 mg, 1.4 mmol), and THF (1 mL). The mixture was heated to 90° C. for 18 h, then cooled and poured into cold water. The resulting precipitate was collected by vacuum filtration to give 10.4 mg (46%) of the desired product as a white solid. $^1$H NMR (300 MHz, DMSO-d$_6$) δ7.18, (m, 3H), 7.78 (m, 5H), 8.53 (bs, 1H), 8.96 (s, 1H), 10.56 (s, 1H); MS (EI) m/z 299.23 (M+H)$^+$.

Example 6

Synthesis of N-(4-Fluoro-phenyl)-6-(2-hydroxy-ethylamino)-1-oxy-nicotinamide

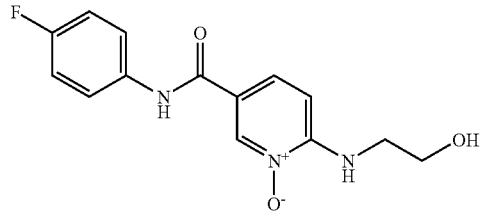

In a sealed tube was placed 6-chloro-N-(4-fluoro-phenyl)-1-oxy-nicotinamide (0.020 g, 0.070 mmole), and ethanolamine (1 mL). The mixture was heated to 90° C. for 18 h, then cooled and poured into cold water. The resulting precipitate was collected by vacuum filtration to give 4.3 mg (21%) of the desired product as a white solid. MS (EI) m/z 292.26 (M+H)$^+$.

Example 7

Synthesis of N-(4-Fluoro-phenyl)-1-oxy-6-pyrrolidin-1-yl-nicotinamide

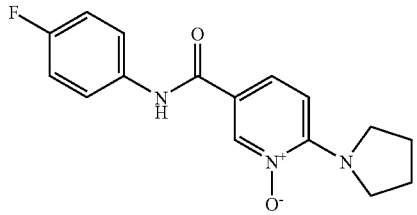

In a sealed tube was placed 6-chloro-N-(4-fluoro-phenyl)-1-oxy-nicotinamide (0.020 g, 0.070 mmole), pyrrolidine (0.031 mL, 0.375 mmol), and THF (1 mL). The mixture was heated to 90° C. for 18 h, then cooled and poured into ethyl acetate. The resulting precipitate was collected by vacuum filtration to give 16.1 mg (70%) of the desired product as a white solid. MS (EI) m/z 302.25 (M+H)$^+$.

Example 8

Synthesis of N-(4-Fluoro-phenyl)-1-oxy-6-pentylamino-nicotinamide

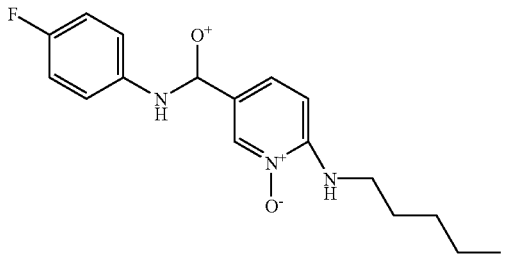

In a sealed tube was placed 6-chloro-N-(4-fluoro-phenyl)-1-oxy-nicotinamide (0.020 g, 0.070 mmole), amylamine (0.043 mL, 0.375 mmol), and THF (1 mL). The mixture was heated to 90° C. for 18 h and then cooled and poured into water. The resulting precipitate was collected by vacuum filtration and purified by trituration with ethyl acetate/methanol to give 16.2 mg (68%) of the desired product as a white solid. MS (EI) m/z 318.28 (M+H)$^+$.

Example 9

Synthesis of 6-Amino-N-(4-Fluoro-phenyl)-1-oxy-nicotinamide

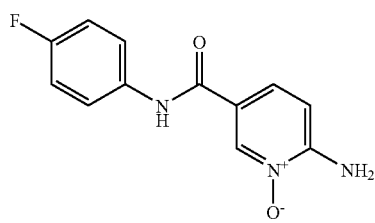

In a sealed tube was placed 6-chloro-N-(4-fluoro-phenyl)-1-oxy-nicotinamide (0.020 g, 0.070 mmole) and ammonium hydroxide (2 mL of a 14.8 M solution in water). The mixture was heated to 90° C. for 18 h and then cooled and the volatiles removed in vacuo. The resulting precipitate was purified by flash chromatography (10% methanol in ammonia saturated dichloromethane to give 9.5 mg (51%) of the desired product as a white solid. MS (EI) m/z 248.25 (M+H)$^+$.

Example 10

6-Bromo-N-(4-fluoro-phenyl)-1-oxy-nicotinamide

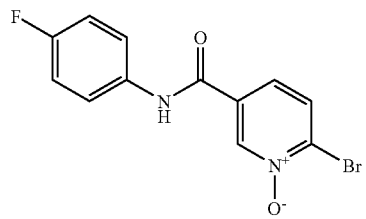

To 8 mL of trifluoracetic acid at 0° C. was added 1 mL of aqueous hydrogen peroxide (30%) over a 5 minute period, followed by the addition of 6-bromo-N-(4-fluoro-phenyl)-nicotinamide (0.1 g, 0.34 mmol) in one portion. The mixture was warmed to 45° C. and stirred for 18 hours. The mixture was cooled diluted with water (1 mL) and concentrated in vacuo. Purification by trituration using hot ethyl acetate produced the desired product as a white solid: MS (EI) m/z 312.89 (M+H)$^+$.

Example 11

N-(4-Fluoro-phenyl)-6-methyl-1-oxy-nicotinamide

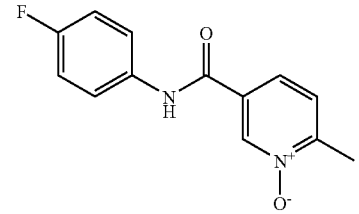

The title compound was prepared in a similar fashion to 2-Chloro-N-(4-fluoro-phenyl)-6-methyl-1-oxy-nicotinamide in Example 14. MS (EI) m/z 247.1 (M+H)$^+$.

Example 12

Synthesis of 6-CHLORO-N-SUBSTITUTED-1-OXY-NICOTINAMIDES

A. 6-Chloro-1-oxy-nicotinic acid

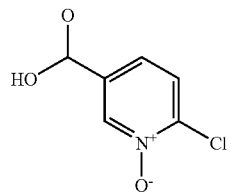

To 400 mL of trifluoracetic acid at 0° C. was added 50 mL of aqueous hydrogen peroxide (30%) over a 5 minute period, followed by the addition of 6-chloro-nicotinic acid (3.07 g, 19.5 mmole) in one portion. The mixture was warmed to 45° C. and stirred for 18 hours, and then 30 mL of additional aqueous hydrogen peroxide (30%) was added in one portion and stirred for 2 h. The mixture was cooled and concentrated in vacuo. Purification by trituration using hot ethyl acetate produced 2.18 g (64%) of the desired product as a white solid: $^1$H NMR (300 MHz, DMSO-$d_6$) $\delta$8.65 (d, 1H, J=1.9 Hz), 7.85 (m, 1H), 7.7 (m, 1H), 3.3 (bs, 1H); MS (EI) m/z 174.13/176.13 (M+H)$^+$.

General Procedure a for the Synthesis of 6-chloro-N-substituted-1-oxy-nicotinamides

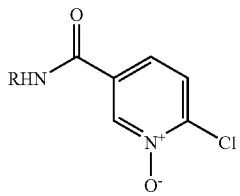

To a suspension of 6-chloro-1-oxy-nicotinic acid (0.040 g, 0.23 mmol) in dry chloroform (5 mL) was added a selected amine (0.3 mmol) followed by the addition of (2-ethyoxy-1-ethoxycarbonyl-1,2-dihydroquinoline, 0.32 mmole). After stirring for 24 hours at room temperature the mixture was diluted with hexanes and the solids isolated by vacuum filtration. Purification of the solids by trituration with ethyl acetate and hexanes afforded the desired 1-oxy-nicotinamides.

Compounds prepared by the general procedure outlined in Example 12 where synthesized from the appropriate amine, as set forth in Table 1.

TABLE 1

N-Benzhydryl-6-chloro-1-oxy-nicotinamide:
MS (EI) m/z 339.21 (M + H)$^+$.
6-Chloro-N-(2-fluoro-phenyl)-1-oxy-nicotinamide:
MS (EI) m/z 267.23 (M + H)$^+$.
6-Chloro-N-(3-chloro-4-fluoro-phenyl)-1-oxy-nicotinamide:
MS (EI) m/z 299.20 (M − H)$^-$.
6-Chloro-N-(4-nitro-phenyl)-1-oxy-nicotinamide:
MS (EI) m/z 292.24 (M − H)$^-$.
N-(3-Bromo-phenyl)-6-chloro-1-oxy-nicotinamide:
MS (EI) m/z 325.16 (M − H)$^-$.
6-Chloro-N-(4-fluoro-3-trifluoromethyl-phenyl)-1-oxy-nicotinamide:

TABLE 1-continued

MS (EI) m/z 333.21 (M − H)$^-$.
6-Chloro-N-(3-fluoro-4-methyl-phenyl)-1-oxy-nicotinamide:
MS (EI) m/z 279.27 (M − H)$^-$.
6-Chloro-N-(3-iodo-phenyl)-1-oxy-nicotinamide:
MS (EI) m/z 373.12 (M − H)$^-$.
3-[(6-Chloro-1-oxy-pyridine-3-carbonyl)-amino]-4-methoxy-benzoic acid:
MS (EI) m/z 323.06 (M + H)$^+$.
6-Chloro-N-(3,4-dimethyl-phenyl)-1-oxy-nicotinamide:
MS (EI) m/z 275.25 (M − H)$^-$.
6-Chloro-N-(3,4-difluoro-phenyl)-1-oxy-nicotinamide:
MS (EI) m/z 283.22 (M − H)$^-$.
N-(4-Benzyloxy-phenyl)-6-chloro-1-oxy-nicotinamide:
MS (EI) m/z 353.23 (M − H)$^-$.
6-Chloro-N-(3-chloro-4-iodo-phenyl)-1-oxy-nicotinamide:
MS (EI) m/z 407.06 (M − H)$^-$.
N-(4-Bromo-3-chloro-phenyl)-6-chloro-1-oxy-nicotinamide:
MS (EI) m/z 361.09 (M − H)$^-$.
N-(4-Bromo-3-methyl-phenyl)-6-chloro-1-oxy-nicotinamide:
MS (EI) m/z 341.15 (M − H)$^-$.
6-Chloro-N-(3-methoxy-phenyl)-1-oxy-nicotinamide:
MS (EI) m/z 277.26 (M − H)$^-$.
N-(4-Bromo-phenyl)-6-chloro-1-oxy-nicotinamide:
MS (EI) m/z 327.11 (M − H)$^-$.
N-(3,5-Bis-trifluoromethyl-phenyl)-6-chloro-1-oxy-nicotinamide:
MS (EI) m/z 383.15 (M − H)$^-$.
6-Chloro-1-oxy-N-(3-trifluoromethoxy-phenyl)-nicotinamide:
MS (EI) m/z 331.19 (M − H)$^-$.
6-Chloro-N-(4-fluoro-3-methyl-phenyl)-1-oxy-nicotinamide:
MS (EI) m/z 279.24 (M − H)$^-$.
6-Chloro-N-(3-fluoro-4-methoxy-phenyl)-1-oxy-nicotinamide:
MS (EI) m/z 295.22 (M − H)$^-$.
6-Chloro-N-(4-methoxy-phenyl)-1-oxy-nicotinamide:
MS (EI) m/z 277.23 (M − H)$^-$.
6-Chloro-1-oxy-N-(4-trifluoromethyl-phenyl)-nicotinamide:
MS (EI) m/z 315.19 (M − H)$^-$.
6-Chloro-N-(2-hydroxy-phenyl)-1-oxy-nicotinamide:
MS (EI) m/z 263.23 (M − H)$^-$.
6-Chloro-N-(4-fluoro-2-methyl-phenyl)-1-oxy-nicotinamide:
MS (EI) m/z 279.24 (M − H)$^-$.
6-Chloro-N-(3,4-dichloro-phenyl)-1-oxy-nicotinamide:
MS (EI) m/z 315.00 (M − H)$^-$.
6-Chloro-N-(3-fluoro-phenyl)-1-oxy-nicotinamide:
MS (EI) m/z 265.11 (M − H)$^-$.
6-Chloro-N-(4-iodo-phenyl)-1-oxy-nicotinamide:
MS (EI) m/z 372.93 (M − H)$^-$.
N-(4-tert-Butyl-phenyl)-6-chloro-1-oxy-nicotinamide:
MS (EI) m/z 303.29 (M − H)$^-$.
6-Chloro-N-(4-chloro-3-trifluoromethyl-phenyl)-1-oxy-nicotinamide:
MS (EI) m/z 349.15 (M − H)$^-$.
6-Chloro-N-(3-chloro-phenyl)-1-oxy-nicotinamide:
MS (EI) m/z 281.19 (M − H)$^-$.
6-Chloro-1-oxy-N-(3-trifluoromethyl-phenyl)-nicotinamide:
MS (EI) m/z 315.20 (M − H)$^-$.
6-Chloro-N-(3-ethoxy-phenyl)-1-oxy-nicotinamide:
MS (EI) m/z 291.25 (M − H)$^-$.
N-(3-Carbamoyl-phenyl)-6-chloro-1-oxy-nicotinamide:
MS (EI) m/z 290.24 (M − H)$^-$.
N-(4-Acetyl-phenyl)-6-chloro-1-oxy-nicotinamide:
MS (EI) m/z 289.24 (M − H)$^-$.
N-benzyl-6-chloro-1-oxy-nicotinamide:
MS (EI) m/z 261.25 (M − H)$^-$.
6-Chloro-N-(4-fluoro-benzyl)-1-oxy-nicotinamide:
MS (EI) m/z 279.24 (M − H)$^-$.
6-Chloro-N-cyclopentyl-1-oxy-nicotinamide:
MS (EI) m/z 241.21 (M + H)$^+$.
6-Chloro-N-cyclohexyl-1-oxy-nicotinamide:
MS (EI) m/z 255.27 (M + H)$^+$.
6-Chloro-N-furan-2-ylmethyl-1-oxy-nicotinamide:
MS (EI) m/z 251.26 (M − H)$^-$.
6-Chloro-1-oxy-N-phenyl-nicotinamide:
MS (EI) m/z 247.26 (M − H)$^-$.
3-[(6-Chloro-1-oxy-pyridine-3-carbonyl)-amino]-benzoic acid tert-butyl ester: MS (EI) m/z 347.27 (M − H)$^-$.
3-[(6-Chloro-1-oxy-pyridine-3-carbonyl)-amino]-benzoic acid:
MS (EI) m/z 291.19 (M − H)$^-$.
3-[(6-Chloro-1-oxy-pyridine-3-carbonyl)-amino]-4-methyl-benzoic acid:
MS (EI) m/z 307.09 (M + H)$^+$.
3-[(6-Chloro-1-oxy-pyridine-3-carbonyl)-amino]-4-methoxy-benzoic acid:
MS (EI) m/z 323.06 (M + H)$^+$.

TABLE 1-continued

5-[(6-Chloro-1-oxy-pyridine-3-carbonyl)-amino]-isophthalic acid:
MS (EI) m/z 337.05 (M + H)+.
3-[(6-Chloro-1-oxy-pyridine-3-carbonyl)-amino]-2,5,6-trifluoro-benzoic
acid: MS (EI) m/z 346.97 (M + H)+.
6-Chloro-1-oxy-N-(3-trifluoromethylsulfanyl-phenyl)-nicotinamide:
MS (EI) m/z 347.13 (M − H)−.
6-Chloro-N-(3-methylsulfanyl-phenyl)-1-oxy-nicotinamide:
MS (EI) m/z 293.19 (M − H)−
N-(4-butyl-phenyl)-6-chloro-1-oxy-nicotinamide:
MS (EI) m/z 303.17 (M − H)−
N-(3-bromo-4-trifluoromethoxy-phenyl)-6-chloro-1-oxy-nicotinamide:
MS (EI) m/z 410.95 (M − H)−.
6-[(6-Chloro-1-oxy-pyridine-3-carbonyl)-amino]-2,3-difluoro-benzoic
acid: MS (EI) m/z 327.07 (M − H)−.
6-Chloro-N-(2,3-difluoro-phenyl)-1-oxy-nicotinamide:
MS (EI) m/z 283.12 (M − H)−.
6-Chloro-N-(4-chloro-phenyl)-1-oxy-nicotinamide:
MS (EI) m/z 281.07 (M − H)−.
6-Chloro-N-(3-cyano-phenyl)-1-oxy-nicotinamide:
MS (EI) m/z 272.08 (M − H)−.
6-Chloro-N-(3,4-dimethoxy-phenyl)-1-oxy-nicotinamide:
MS (EI) m/z 307.09 (M − H)−.
6-Chloro-1-oxy-N-(3,4,5-trimethoxy-phenyl)-nicotinamide:
MS (EI) m/z 337.07 (M − H)−.
6-Chloro-1-oxy-N-(4-thiocyanato-phenyl)-nicotinamide:
MS (EI) m/z 304.05 (M − H)−.
4-[(6-Chloro-1-oxy-pyridine-3-carbonyl)-amino]-benzoic acid methyl
ester: MS (EI) m/z 305.05 (M − H)−.
6-Chloro-N-(3,3-dimethyl-butyl)-1-oxy-nicotinamide:
MS (EI) m/z 255.18 (M − H)−.
6-Chloro-N-(2,4-difluoro-benzyl)-1-oxy-nicotinamide:
MS (EI) m/z 297.12 (M − H)−.
6-Chloro-1-oxy-N-(4-trifluoromethoxy-phenyl)-nicotinamide:
MS (EI) m/z 331.18 (M − H)−.
5-[(6-Chloro-1-oxy-pyridine-3-carbonyl)-amino]-2-hydroxy-benzoic acid:
m/z 307.07 (M − H)−.
6-Chloro-N-(3,4-difluoro-benzyl)-1-oxy-nicotinamide:
m/z 297.13 (M − H)−.
6-Chloro-N-(2-methylsulfanyl-phenyl)-1-oxy-nicotinamide:
m/z 295.07 (M + H)+.
6-Chloro-N-(4-methylsulfanyl-phenyl)-1-oxy-nicotinamide:
m/z 295.04 (M + H)−.

Example 13

Synthesis of 2,6-Dichloro-N-(4-fluoro-phenyl)-1-oxy-nicotinamide

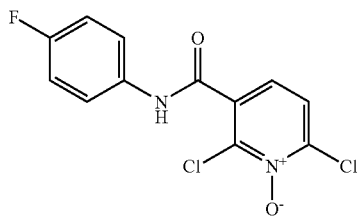

To 16 mL of trifluoracetic acid at 0° C. was added 2 mL of aqueous hydrogen peroxide (30%) over a 5 minute period followed by the addition of 2,6-dichloro-N-(4-fluoro-phenyl)-nicotinamide (0.107 g, 0.377 mmole) in one portion. The mixture was warmed to room temperature and stirred for 18 hours. The mixture was concentrated in vacuo. Purification by trituration using hot ethyl acetate produced 8 mg (7%) of the desired product as a white solid: MS (EI) m/z 299.16 (M−H)−.

Example 14

Synthesis of 2-Chloro-N-(4-fluoro-phenyl)-6-methyl-1-oxy-nicotinamide

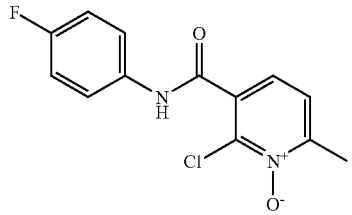

To 8 mL of trifluoracetic acid at 0° C. was added 1 mL of aqueous hydrogen peroxide (30%) over a 5 minute period followed by the addition of 2-chloro-N-(4-fluoro-phenyl)-6-methyl-nicotinamide (0.100 g, 0.379 mmole) in one portion. The mixture was warmed to 50° C. and stirred for 18 hours, and then 1 mL of additional aqueous hydrogen peroxide (30%) was added in one portion and stirred for 24 h. The mixture was cooled and concentrated in vacuo. Purification by reverse phase HPLC produced 4 mg (4%) of the desired product as a white solid: MS (EI) m/z 279.15 (M−H)−.

Example 15

Synthesis of 5,6-Dichloro-N-(4-fluoro-phenyl)-1-oxy-nicotinamide

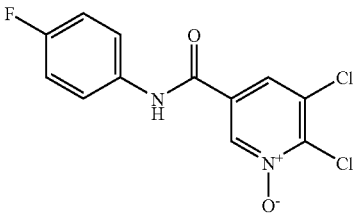

To 8 mL of trifluoracetic acid at 0° C. was added 1 mL of aqueous hydrogen peroxide (30%) over a 5 minute period followed by the addition of 5,6-dichloro-N-(4-fluoro-phenyl)-nicotinamide (0.100 g, 0.35 mmole) in one portion. The mixture was warmed to 50° C. and stirred for 18 hours, and then 1 mL of additional aqueous hydrogen peroxide (30%) was added in one portion and stirred for 24 h. The mixture was cooled and concentrated in vacuo. Purification by trituration using methanol/ethyl acetate produced 11 mg (10%) of the desired product as a white solid: 299.14 (M−H)−.

Example 16

Synthesis of N-(4-Fluoro-phenyl)-6-methoxy-1-oxy-nicotinamide

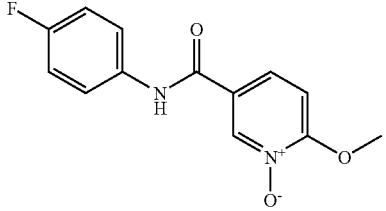

To a suspension of 6-chloro-N-(4-fluoro-phenyl)-1-oxy-nicotinamide (0.040 g, 0.15 mmole) in dry tetrahydrofuran (1 mL) was added sodium methoxide (0.024 g, 0.045 mmol) and dry methanol (0.5 mL). After stirring for 1 hour at room temperature additional sodium methoxide (0.024 g, 0.045 mmol) was added and stirred for 15 minutes. The mixture was diluted with ethyl acetate (20 mL) and washed with water. The combined organic extracts were dried over anhydrous sodium sulfate, filtered, and concentrated in vacuo. Purification by trituration using ethyl acetate gave 18 mg (46%) of the desired product as a white solid. MS (EI) m/z 263.21 (M+H)$^+$.

Example 17

Synthesis of N-(4-Fluoro-phenyl)-6-methylsulfanyl-1-oxy-nicotinamide

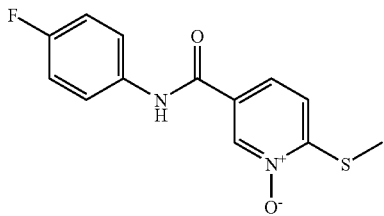

To a suspension of 6-chloro-N-(4-fluoro-phenyl)-1-oxy-nicotinamide (0.033 g, 0.12 mmole) in dry tetrahydrofuran (1 mL) was added sodium thiomethoxide (0.013 g, 0.18 mmol). After stirring for 1 h at room temperature the mixture was diluted with ice water and the solids isolated by vacuum filtration to provide 26 mg (79%) of the desired product as a white solid. MS (EI) m/z 277.17 (M−H)$^-$.

Example 18

Synthesis of 6-Ethylsulfanyl-N-(4-fluoro-phenyl)-1-oxy-nicotinamide

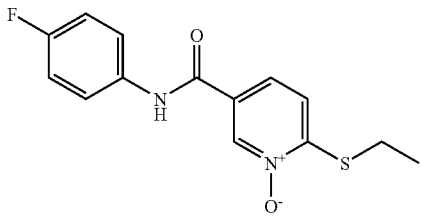

To a suspension of 6-chloro-N-(4-fluoro-phenyl)-1-oxy-nicotinamide (0.102 g, 0.38 mmole) in dry tetrahydrofuran (4 mL) was added sodium thioethoxide (0.080 g, 0.96 mmol). The mixture was stirred for 3 hours. Approximately half of the volatiles were removed in vacuo and the remaining solids diluted with ice water and the solids isolated by vacuum filtration. The solids were purified by trituration using ethyl acetate/methanol to provide 37 mg (37%) of the desired product as a white solid. MS (EI) m/z 291.14 (M−H)$^-$.

Example 19

Synthesis of 6-Dimethylamino-N-(4-fluoro-phenyl)-nicotinamide N-oxide

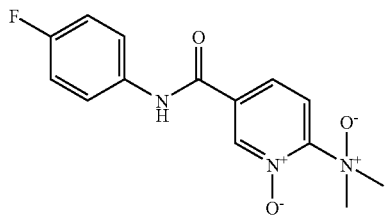

To a solution of 6-dimethylamino-N-(4-fluoro-phenyl)-nicotinamide (0.027 g, 0.11 mmol, prepared as in Example 1) in 2 mL of dry dichloromethane/methanol (4:1) was added 3-chloroperoxybenzoic acid (0.020 g, 0.12 mmol) at 0° C. The reaction mixture was then heated to reflux and additional 3-chloroperoxybenzoic acid (0.040 g, 0.24 mmol) was added. After heating for a total of 7 h the reaction mixture was cooled, diluted with chloroform and washed with aqueous sodium carbonate (1M), dried over sodium sulfate, and concentrated in vacuo. Purification by flash chromatography, using 10% methanol/dichloromethane saturated with ammonia, yielded 4 mg (13%) of the desired product as a white solid. MS (EI) m/z 274.18 (M−H)$^-$.

Example 20

Synthesis of 6-Ethanesulfonyl-N-(4-fluoro-phenyl)-1-oxy-nicotinamide

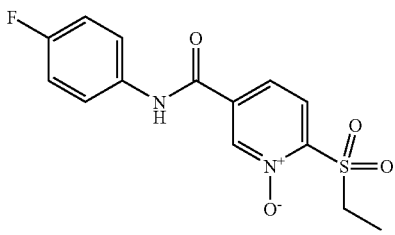

A. 6-Ethylsulfanyl-N-(4-fluoro-phenyl)-nicotinamide

Into a round-bottomed flask equipped with a condenser was placed 6-chloro-N-(4-fluoro-phenyl)-nicotinamide (0.20 g, 0.80 mmol), tetrahydrofuran (6 mL), and sodium thioethoxide (0.10 g, 1.2 mmol). The mixture was heated to reflux for 4 h at which time additional sodium thioethoxide (0.10 g, 1.2 mmol) was added and stirred for 2 additional hours. The reaction mixture was then cooled and poured into ice water and the solids isolated by vacuum filtration to provide 0.15 g (68%) of the product as a white solid. MS (EI) m/z 275.2 (M−H)$^-$.

B. 6-Ethanesulfonyl-N-(4-fluoro-phenyl)-1-oxy-nicotinamide

To 8 mL of trifluoracetic acid at 0° C. was added 1 mL of aqueous hydrogen peroxide (30%) over a 5 minute period followed by the addition of 6-ethylsulfanyl-N-(4-fluoro-phenyl)-nicotinamide (0.050 g, 0.18 mmol) in one portion. The mixture was warmed to room temperature and stirred for 18 h. Approximately half of the volatiles were removed in vacuo and the remaining solids diluted with ice water and the solids isolated by vacuum filtration to provide 0.031 g (53%) of the product as a white solid. MS (EI) m/z 323.07 (M−H)⁻.

The compounds listed in Table 2 were prepared from 6-chloro-N-(4-fluoro-phenyl)-nicotinamide and the appropriate thiolate in the same manner as 6-ethanesulfonyl-N-(4-fluoro-phenyl)-1-oxy-nicotinamide:

TABLE 2

N-(4-Fluoro-phenyl)-6-methanesulfonyl-1-oxy-nicotinamide:
MS (EI) m/z 309.20 (M − H)⁻.
N-(4-Fluoro-phenyl)-1-oxy-6-(propane-2-sulfonyl)-nicotinamide:
MS (EI) m/z 337.14 (M − H)⁻.
N-(4-Fluoro-phenyl)-1-oxy-6-(propane-1-sulfonyl)-nicotinamide:
MS (EI) m/z 337.15 (M − H)⁻.
N-(4-Fluoro-phenyl)-1-oxy-6-phenylmethanesulfonyl-nicotinamide:
MS (EI) m/z 385.23 (M − H)⁻.
6-Cyclopentanesulfonyl-N-(4-fluoro-phenyl)-1-oxy-nicotinamide:
MS (EI) m/z 363.20 (M − H)⁻.
3-[5-(4-Fluoro-phenylcarbamoyl)-1-oxy-pyridine-2-sulfonyl]-benzoic acid:
MS (EI) m/z 415.10 (M − H)⁻.
3-[5-(4-Fluoro-phenylcarbamoyl)-1-oxy-pyridine-2-sulfonyl]-propionic
acid: MS (EI) m/z 367.17 (M − H)⁻.
N-(4-Fluoro-phenyl)-1-oxy-6-(2,3,5,6-tetrafluoro-benzenesulfonyl)-
nicotinamide: MS (EI) m/z 443.17 (M − H)⁻.
N-(4-Fluoro-phenyl)-1-oxy-6-(toluene-3-sulfonyl)-nicotinamide:
MS (EI) m/z 385.29 (M − H)⁻.
6-(4-Fluoro-benzenesulfonyl)-N-(4-fluoro-phenyl)-1-oxy-nicotinamide:
MS (EI) m/z 389.27 (M − H)⁻
6-Benzenesulfonyl-N-(4-fluoro-phenyl)-1-oxy-nicotinamide:
MS (EI) m/z 371.18 (M − H)⁻.

Example 21

Biological Activities of Representative Nicotinalide-N-Oxides

The IL-8 and GRO-α chemokine inhibitory effects of compounds of the present invention were determined by the following in vitro assays:

Preparation of PMNs

Peripheral blood from healthy human volunteers was collected into heparin, diluted in an equal volume of PBS, layered over Ficoll-Paque Plus (Pharmacia Biotech, Uppsala, Sweden), and spun at 400×g for 30 min. The PMN rich fraction was removed and residual erythrocytes were lysed with hypotonic saline. The polymorphonuclear neutrophils (PMNs) were washed once with assay buffer (Dulbecco's PBS containing divalent cations and 0.1% endotoxin-free BSA), and resuspended at 1E7 cells/mL in the same buffer. PMNs were loaded with 5 μM calcein AM (Molecular Probes, Eugene, Oreg.), washed twice and resuspended in assay buffer.

Chemotaxis Assay

Chemotaxis assays with test compounds of the present invention were generally performed according to the method described by Frevert et al., J. Immunol. Meth. 213:41–52 (1998) using either GRO-α or IL-8 as summarized below.

Growth Regulatory Oncogene a (GRO-α) driven chemotaxis assays were performed according to the following protocol. The lower chambers of a ChemoTx plate (Neuro Probe, Gaithersburg, Md.) were filled with 29 μL of 50 nM GRO-α (PeproTech, Rocky Hill, N.J.) and test compound. The empty upper chambers were affixed to the lower (plate), and 25 μL of PMN suspension (3E6 cells/mL), without (control) or with 0.04–40 μM test compound, preincubated 30 min, was added to the upper wells. Test compounds were dissolved in DMSO (100%) at 20 mM and diluted in assay buffer to the desired concentrations; final DMSO concentration was 0.2%. Neutrophil migration proceeded for 40 min at 37° C. in a humidified incubator with 5% $CO_2$. After removing nonmigrated cells from the top of the plate, migrated cells were quantified by reading fluorescence on a Wallac Victor.

Maximum chemotactic response was determined by cells to which no compound was added (positive control), whereas the negative control (unstimulated) was defined by the absence of chemokine in the lower chamber. The ratio of the positive to negative controls represents the chemotactic index of the cells. The results from this assay are reported in Tables 3–5, under the column headings IL-8 and GRO-α, and under the sub-column headings ChTx (for chemotaxis).

Binding Assays

[$^{125}$I] IL-8 (human recombinant) was obtained from NEN Life Science Products, Inc., Boston, Mass., with specific activity of 2200 Ci/mmol. Recombinant human IL-8 was obtained from R&D Systems, Minneapolis, Minn. IL-8 type β receptor membranes were prepared from human Sf9 cells co-expressed with Gαi3β1γ2 proteins by BioSignal™, Montreal, Canada. Wheat Germ Agglutinin Scintillation Proximity Assay Beads were obtained from Amersham Pharmacia Biotech, Piscataway, N.J. All assays were performed in a 96-well, solvent resistant, white PicoPlate obtained from Packard Instruments. Each reaction mixture contained [$^{125}$I] IL-8 (0.16 nM), 5 μg/well IL-8Rβ and 1 mg/well WGA-SPA beads in 25 mM Hepes (pH 7.4), containing 2 mM $CaCl_2$, 1 mM $MgCl_2$, 0.1% BSA and 0.03% CHAPS. In addition, drug or compound of interest was added which had been pre-dissolved in DMSO so as to reach a final concentration of between 0.01 nM and 80 μM, with a maximum final DMSO concentration of 1%. Nonspecific binding was defined by the presence of 8–16 nM unlabelled IL-8. The assay was initiated by the addition of WGA-SPA beads in 25 mM Hepes (pH 7.4) containing 2 mM $CaCl_2$ and 1 mM $MgCl_2$. After 4–6 hours of gentle agitation at room temperature, the plate was counted on the Packard TopCount liquid scintillation counter.

Selected compounds were screened by Panlabs (Bothell Wash.) using their CXCR2 filtermat binding assay. This assay measures binding of [$^{125}$I]Interleukin-8 to human interleukin-CXCR2 (IL8RB) receptors and is also described in Ahuja, S. K. and Murphy, P. M., J. Biol. Chem. 271: 20545–20550, 1996. In summary, CHO cells stably transfected with a plasmid encoding the human CXCR2 (IL8RB) chemokine receptor were used to prepare membranes in modified HEPES pH 7.4 buffer. A 2 μg aliquot of membrane was incubated with 15 pM [$^{125}$I]Interleukin-8 for 60 minutes at room temperature. Non-specific binding was estimated in the presence of 10 nM interleukin-8. Membranes were filtered and washed 3 times and the filters were counted to determine [$^{125}$I]Interleukin-8 specifically bound. Compounds were screened at 10 μM and results are reported in terms of Specific Binding (%) in Tables 3–5.

Reference Data:

| Compound | $IC_{50}$ (nM) | Ki (nM) | nH |
|---|---|---|---|
| GROα (or MGSA) | 0.098 | 0.098 | 0.9 |
| Interleukin-8* | 0.035 | 0.024 | 0.7 |
| NAP-2 | 3.1 | 2.2 | 0.6 |

MGSA = Melanoma Growth Stimulatory Activity;
*Indicates standard reference agent used;
NAP-2 = Neutrophil Activating Peptide-2

Data obtained by the above-described assays are reported in Tables 3–5. Binding assay results and ChTx (%) results are reported as "*" for % values of less than or equal to 40, and "**" for % values greater than 40. When no value appears in a cell, the relevant test was not performed.

The compounds referred to in Table 3 have the following basic structure, and vary only in the identity of $R^1$.

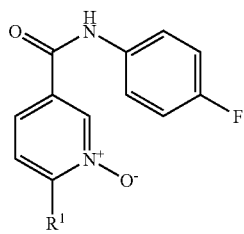

The compounds referred to in Table 4 have the following basic structure, and vary only in the identity of $R^2$ and $R^3$.

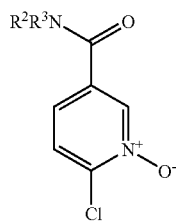

The compounds having test results presented in Table 5 are shown in their entireties within that Table, with the proviso that PhF represents para-fluorophenyl.

TABLE 3

| $R^1$ | IL-8 Binding @ 20 uM, % | GRO-α ChTx @ 20 μM, % |
|---|---|---|
| Cl— | **(1) | ** |
| (CH₃)₂N— | * | * |
| PhCH₂NH— | * | * |
| PhNH— | ** | * |
| CH₃NH— | ** | ** |
| imidazol-1-yl | * | * |

TABLE 3-continued

| $R^1$ | IL-8 Binding @ 20 uM, % | GRO-α ChTx @ 20 μM, % |
|---|---|---|
| HOCH₂CH₂NH— | * | ** |
| CH₃(CH₂)₄NH— | * | ** |
| pyrrolidin-1-yl | * | * |
| H₂N— | * | * |
| CH₃SO₂— | ** | ** |
| CH₃O— | * | ** |
| CH₃S— | ** | ** |
| PhSO₂— | ** | ** |
| CH₃CH₂S— | * | * |
| CH₃CH₂SO₂— | ** | ** |
| (CH₃)₂CHSO₂— | ** | ** |
| CH₃CH₂CH₂SO₂— | ** | ** |

TABLE 3-continued
| R¹ | IL-8 Binding @ 20 uM, % | GRO-α ChTx @ 20 μM, % |
|---|---|---|
| 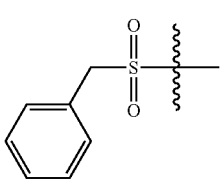 |  |  |
| 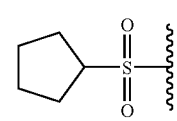 |  |  |
| 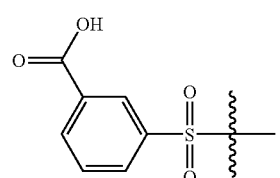 | ** | * |
| 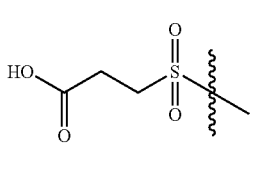 | ** | * |
| 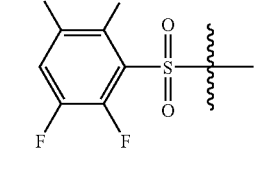 | ** | * |
| 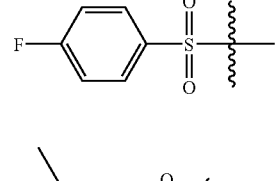 |  |  |
| 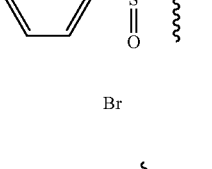 | * | ** |
| Br | | ** |
|  | *(2) | * |
(1) by the Panlabs assay, this compound also received a rating of "**".
(2) by the Panlabs assay, this compound received a rating of "**".
TABLE 4
| —NR²R³ | IL-8 Binding @ 20 uM, % | GRO-α ChTx @ 20 μM, % |
|---|---|---|
| 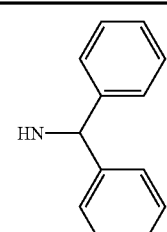 | * | ** |
| 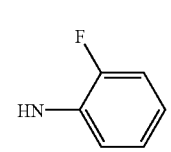 | * | ** |
| 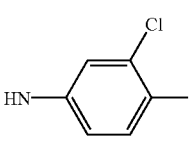 | * | ** |
| 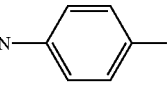 | * | ** |
|  | * | ** |
| 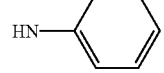 | * | ** |
| 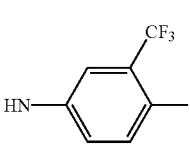 | * | * |
| 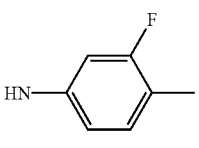 | * | ** |
| 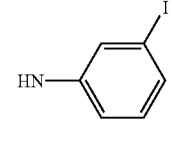 | * | * |
| 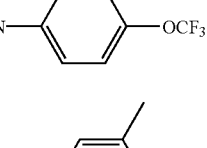 | * | * |

TABLE 4-continued

| —NR²R³ | IL-8 Binding @ 20 uM, % | GRO-α ChTx @ 20 μM, % |
|---|---|---|
| HN—(3,4-difluorophenyl) | * | ** |
| HN—(4-benzyloxyphenyl) | * | ** |
| HN—(3-chloro-4-iodophenyl) | * | ** |
| HN—(3-chloro-4-bromophenyl) | * | ** |
| HN—(3-methyl-4-bromophenyl) | * | ** |
| HN—(3-methoxyphenyl) | * | ** |
| HN—(3,5-bis(trifluoromethyl)phenyl) | * | * |
| HN—(4-bromophenyl) | ** | ** |
| HN—(3-trifluoromethoxyphenyl) | * | * |
| HN—(3-methyl-4-fluorophenyl) | * | * |
| HN—(3-fluoro-4-methoxyphenyl) | * | * |
| HN—(4-methoxyphenyl) | * | * |
| HN—(4-trifluoromethylphenyl) | * | * |
| HN—(2-hydroxyphenyl) | * | * |
| HN—(2-methyl-4-fluorophenyl) | * | ** |
| HN—(3,4-dichlorophenyl) | * | ** |
| HN—(3-fluorophenyl) | * | ** |
| HN—(4-iodophenyl) | * | ** |
| HN—(4-tert-butylphenyl) | * | ** |
| HN—(3-trifluoromethyl-4-chlorophenyl) | * | ** |
| HN—(3-chlorophenyl) | * | ** |

TABLE 4-continued

| —NR²R³ | IL-8 Binding @ 20 uM, % | GRO-α ChTx @ 20 μM, % |
|---|---|---|
| HN—C₆H₄-3-CF₃ | * | ** |
| HN—C₆H₄-3-OEt | * | C* |
| HN—C₆H₄-3-C(O)NH₂ | * | * |
| HN—C₆H₄-4-C(O)CH₃ | * | * |
| HN—CH₂—C₆H₅ | * | * |
| HN—CH₂—C₆H₄-4-F | * | * |
| HN—cyclopentyl | * | * |
| HN—cyclohexyl | * | * |
| HN—CH₂-(2-furyl) | * | * |
| HN—C₆H₅ | | ** |
| HN—C₆H₄-3-C(O)O-tBu | | ** |

| —NR²R³ | IL-8 Binding @ 20 uM, % | GRO-α ChTx @ 20 μM, % |
|---|---|---|
| HN—C₆H₄-3-COOH | | * |
| HN—C₆H₃-3-COOH-4-Me | | ** |
| HN—C₆H₃-3-COOH-4-OMe | | ** |
| HN—C₆F₃-COOH | | * |
| HN—C₆H₃-3-COOH-4-OH | | * |
| HN—C₆H₃-COOH-F₂ | | ** |
| HN—C₆H₃-3,5-(COOH)₂ | | * |

TABLE 4-continued
| —NR²R³ | IL-8 Binding @ 20 uM, % | GRO-α ChTx @ 20 µM, % |
|---|---|---|
| 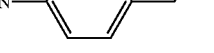 | | ** |
| 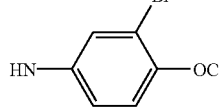 | | * |
| 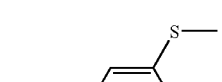 | | ** |
| 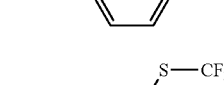 | | ** |
| 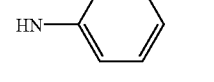 | | ** |
| 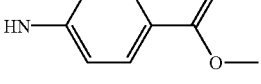 | | ** |
| 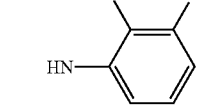 | | ** |
| 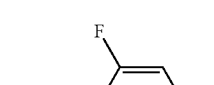 | | * |
| 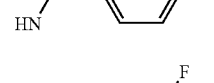 | | * |
| 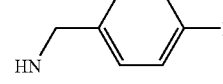 | | ** |
| 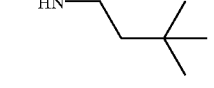 | | ** |
TABLE 4-continued
| —NR²R³ | IL-8 Binding @ 20 uM, % | GRO-α ChTx @ 20 µM, % |
|---|---|---|
| 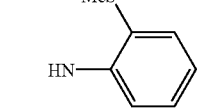 | | ** |
| (3-CN aniline) | | ** |
| (4-SCN aniline) | | * |
| (3,4,5-trimethoxy aniline) | | * |
| (3,4-dimethoxy aniline) | | * |
TABLE 5
| Structure | GRO-α ChTx @ 20 µM, % |
|---|---|
| 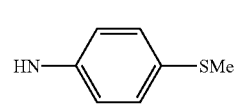 (2,6-dichloro pyridine N-oxide carboxamide with PhF) | ** |
| (5,6-dichloro pyridine N-oxide carboxamide with PhF) | ** |

TABLE 5-continued

| Structure | GRO-α ChTx @ 20 µM, % |
|---|---|
| [Structure: pyridine N-oxide with PhF-NH-C(O)-, Cl, CH3 substituents] | * |

Example 22

Biological Activities of Representative Nicotinalide-N-Oxides

Selected N-oxide compounds were tested in the five biological assays as described below, with the results provided in Table 6. In Table 6, "*" indicates a value of less than or equal to 40, while "**" indicates a value of greater than 40. These biological activities were measured at Panlabs (Bothell, Wash.).

CCR5 Assay (Chemokine CCR5 (Human))

This assay measures the binding of [$^{125}$I]MIP-1β to human chemokine CCR5 receptors. See Samson, M., et al., *J. Biol. Chem.* 272:24934–24941, 1997. In brief, CHO-K1-$_p$ 242-CCR5 cells stably transfected with a plasmid encoding the human chemokine CCR5 receptor were used to prepare membranes in modified HEPES buffer at pH 7.4 using standard techniques. A 1 µg aliquot was incubated with 0.1 nM [$^{125}$I]MIP-1β for 120 minutes at 25° C. Non-specific binding was estimated in the presence of 0.1 µM MIP-1β. Membranes were filtered and washed 3 times and filters were counted to determine [$^{125}$I]MIP-1β specifically bound. Compounds were screened at 10 µM. The data obtained from this assay is reported in Table 6 (row titled "CCR5"), in terms of specific binding (%).

Reference Data:

| Compound | IC$_{50}$ (nM) | Ki (nM) | nH |
|---|---|---|---|
| MIP-1α | 0.039 | 0.030 | 0.8 |
| *MIP-1β | 0.074 | 0.057 | 0.9 |
| RANTES | 0.012 | 0.0093 | 0.9 |

*Indicates standard reference agent used.
MIP = microphage inflammatory protein.
RANTES = regulated on activation of normal T-cell expressed and secreted CXCR1 Assay (Chemokine CXCR1/Interleukin IL-8$_A$ (Human))

This assay measures binding of [$^{125}$I]Interleukin-8 to human interleukin-CXCR1 (ILR8A) receptors. See Ahuja, S. K. and Murphy, P. M. *J. Biol. Chem.* 271:20545–20550, 1996 for details. In brief, CHO cells stably transfected with a plasmid encoding the human CXCR1 (IL8RA) chemokine receptor were used to prepare membranes in modified HEPES pH 7.4 buffer using standard techniques. A 5 µg aliquot of membrane was incubated with 8 pM [$^{125}$I]Interleukin-8 for 60 minutes at room temperature. Non-specific binding was estimated in the presence of 10 nM interleukin-8. Membranes were filtered and washed 3 times and the filters were counted to determine [$^{125}$I]Interleukin-8 specifically bound. Compounds were screened at 10 µM, with the data reported in Table 6 (row titled "CXCR1") in terms of specific binding (%).

Reference Data:

| Compound | IC$_{50}$ (nM) | Ki (nM) | nH |
|---|---|---|---|
| GROα (or MGSA) | >10,000 | — | — |
| *Interleukin-8 | 0.035 | 0.007 | 1.0 |
| NAP-2 | >10,000 | — | — |

*Indicates standard reference agent used.
GROα = Growth Regulatory Oncogene α.
MGSA = Melanoma Growth Stimulatory Activity.
NAP-2 = Neutrophil Activating Peptide-2

CXCR2 Assay (Chemokine CXCR2/Interleukin IL-8B (Human))

This assay measures binding of [$^{125}$I]Interleukin-8 to human interleukin-CXCR2 (IL8RB) receptors. See Ahuja, S. K. and Murphy, P. M., *J. Biol. Chem.* 271: 20545–20550, 1996, for details. In brief, CHO cells stably transfected with a plasmid encoding the human CXCR2 (IL8RB) chemokine receptor were used to prepare membranes in modified HEPES pH 7.4 buffer using standard techniques. A 2 µg aliquot of membrane was incubated with 15 pM [$^{125}$I] Interleukin-8 for 60 minutes at room temperature. Non-specific binding was estimated in the presence of 10 nM interleukin-8. Membranes were filtered and washed 3 times and the filters were counted to determine [$^{125}$I]Interleukin-8 specifically bound. Compounds were screened at 10 µM, with the results reported in Table 6 (row titled "CXCR2") in terms of specific binding (%).

Reference Data:

| Compound | IC$_{50}$ (nM) | Ki (nM) | nH |
|---|---|---|---|
| GROα (or MGSA) | 0.098 | 0.068 | 0.9 |
| *Interleukin-8 | 0.035 | 0.024 | 0.7 |
| NAP-2 | 3.1 | 2.2 | 0.6 |

*Indicates standard reference agent used.
GROα = Growth Regulatory Oncogene α.
MGSA = Melanoma Growth Stimulatory Activity.
NAP-2 = Neutrophil Activating Peptide-2.

NPY$_1$ Assay (Neuropeptide Y$_1$ (Human))

This assay measures binding of [$^{125}$I]Peptide YY (PYY) to human neuropeptide Y$_1$ (NPY$_1$) receptors. See Fuhlendorff, J., et al. *Proc. Natl Acad. Sci. USA* 87:182–186, 1990 and Sheikh, S. P., et al. *J. Biol. Chem.* 264: 6648–6654, 1989. In brief, SK-N-MC (human neuroblastoma) cells were used in modified HBSS pH 7.4 buffer using standard techniques. The cells (10$^6$) were incubated with 12.5 pM [$^{125}$I] PYY for 45 minutes at 25° C. Non-specific binding was estimated in the presence of 0.1 µM NPY (human, rat). Cells were centrifuged and pellets were counted to determine [$^{125}$I]PYY specifically bound. Compounds were screened at 10 µM, with the results shown in Table 6 (row titled "NPY$_1$"), reported in terms of specific binding (%).

Reference Data:

| Compound | IC$_{50}$ (nM) | Ki (nM) | nH |
|---|---|---|---|
| *NPY (human, rat) | 4.0 | 3.9 | 1.0 |
| NPY (porcine) | 7.8 | 7.6 | 0.9 |
| NPY (13–36) | 2,200 | 2,100 | 1.1 |

*Indicates standard reference agent used.

Somatostatin Assay

This assay measures binding of [$^{125}$I]tyr$^1$ Somatostatin to somatostatin receptors. See Thermos, K. and Reisine, T. *Mol. Pharmacol.* 33:370–377, 1988, and Srikant, C. B. and Heisler, S., *Endocrinology* 117:271–278, 1985. In brief, AtT-20 (mouse pituitary) cells were used to prepare membranes in modified Tris-HCl pH 7.5 buffer using standard techniques. A 200 μg aliquot of membrane was incubated with 0.04 nM [$^{125}$I]tyr$^1$ Somatostatin for 60 minutes at 25° C. Non-specific binding was estimated in the presence of 1 μM somatostatin-14. Membranes were filtered and washed 3 times and the filters were counted to determine [$^{125}$I]tyr$^1$ Somatostatin specifically bound. Compounds were screened at 10 μM, with the data reported in Table 6 (row titled "Somat.") in terms of specific binding (%).

Reference Data:

| Compound | IC$_{50}$ (nM) | Ki (nM) | nH |
|---|---|---|---|
| *Somatostatin | 0.93 | 0.54 | 0.8 |
| D-Trp$^8$ Somatostatin | 0.23 | 0.13 | 1.1 |

*Indicates standard reference agent used.

TABLE 6

| Structure |
|---|
|  |

| Assay | | | | |
|---|---|---|---|---|
| CCR5 |  | ** | * | ** |
| CXCR1 | ** | ** | ** | * |
| CXCR2 | ** | ** | ** | ** |
| NPY$_1$ | * | ** | * | ** |
| Somat. | * | ** | * | * |

| Structure |
|---|
|  |

Assay

TABLE 6-continued

| | | | | | |
|---|---|---|---|---|---|
| CCR5 | ** | * | ** | * | * |
| CXCR1 | * | * | * | * | ** |
| CXCR2 | ** | ** | ** | ** | ** |
| $NPY_1$ | ** | * | * | | |
| Somat. | * | | * | | * |

All references cited herein are hereby incorporated by reference.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A compound having the structure (I):

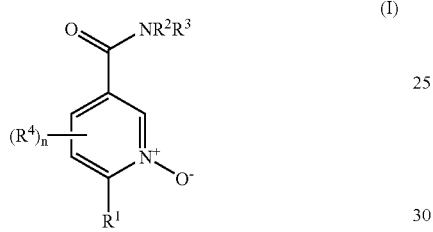

(I)

and optical isomers, diastereomers, enantiomers and pharmaceutically acceptable salts thereof, wherein $R^1$ is $R^5$—$SO_2$— and $R^5$ is selected from alkyl, $(CH_2)_2$—COOH, aryl, carbocycle, aryl(alkylene), and carbocycle(alkylene)

$R^2$ is hydrogen;

$R^3$ is substituted or unsubstituted aryl or substituted or unsubstituted aryl(alkylene);

$R^4$ is selected from halogen, substituted or unsubstituted aryl, substituted or unsubstituted heteroaryl, substituted or unsubstituted carbocycle aliphatic ring, substituted or unsubstituted amino, or hydroxy, wherein, when $R^4$ is halogen, it is not para to the N-oxide group; and n is 0 or 1.

2. The compound of claim 1 wherein $R^1$ is selected from $(C_1$–$C_6$alkyl$)SO_2$—, $PhSO_2$—, fluorinatedphenyl$SO_2$—, $PhCH_2SO_2$—, cyclopentyl$SO_2$—, m-carboxyphenyl$SO_2$—, m-methylphenyl$SO_2$—, and HOOC—$(C_1$–$C_4$alkylene)$SO_2$—.

3. The compound of claim 1 having the structure (II)

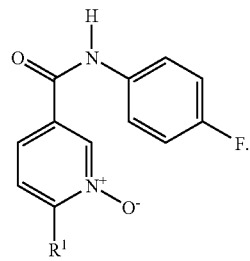

(II)

wherein $R^1$ is selected from $(C_1$–$C_6$alkyl$)SO_2$—, $PhSO_2$—, fluorinatedphenyl$SO_2$—, $PhCH_2SO_2$—, cyclopentyl$SO_2$—, m-carboxyphenyl$SO_2$—, m-methylphenyl$SO_2$—, and HOOC—$(C_1$–$C_4$alkylene)$SO_2$—.

4. A compound that is 6-ethanesulfonyl-N-(4-fluorophenyl)-1-oxynicotinamide.

* * * * *